US006511676B1

(12) United States Patent
Boulikas

(10) Patent No.: US 6,511,676 B1
(45) Date of Patent: Jan. 28, 2003

(54) THERAPY FOR HUMAN CANCERS USING CISPLATIN AND OTHER DRUGS OR GENES ENCAPSULATED INTO LIPOSOMES

(76) Inventor: Teni Boulikas, 249 Matadero Ave., Palo Alto, CA (US) 94306

( * ) Notice: Subject to any disclaimer, the term of this patent is extended or adjusted under 35 U.S.C. 154(b) by 0 days.

(21) Appl. No.: 09/434,345

(22) Filed: Nov. 5, 1999

(51) Int. Cl.[7] .............................................. A61K 9/127
(52) U.S. Cl. ......................... 424/450; 264/4.1; 264/4.3
(58) Field of Search ........................... 424/450; 264/4.1, 264/4.3

(56) References Cited

U.S. PATENT DOCUMENTS

| | | | |
|---|---|---|---|
| 5,213,804 A | * 5/1993 | Martin et al. ................. 424/450 |
| 5,334,761 A | * 8/1994 | Gebeyehu et al. ........... 564/197 |
| 5,393,530 A | 2/1995 | Schneider et al. |
| 5,567,434 A | 10/1996 | Szoka |
| 5,747,469 A | 5/1998 | Roth et al. |
| 5,795,589 A | 8/1998 | Mayer et al. |
| 5,843,475 A | * 12/1998 | Perez-Soler et al. ......... 424/450 |
| 5,882,679 A | 3/1999 | Needham |
| 5,894,060 A | 4/1999 | Boulikas |
| 5,908,777 A | 6/1999 | Lee et al. |
| 5,945,122 A | 8/1999 | Abra et al. |
| 6,028,066 A | * 2/2000 | Unger .......................... 514/180 |
| 6,126,966 A | * 10/2000 | Abra et al. .................... 424/450 |

OTHER PUBLICATIONS

Speelmans, G. et al. "The interaction of the anti–cancer drug cisplatin with phospholipids is specific for negatively charged phsopholipids and takes place at low chloride ion concentration" *Biochim. Biophys. ACTA* (1996) 1283:60–66.

Boulikas, T., "Evolutionary consequences of nonrandom damage and repair of chromatin domains" *J. Mol. Evol.* 35:156–180 (1992).

Boulikas, T., "DNA lesion–recognizing proteins and the p53 connection" *Anticancer Res.* 16:225–242 (1996).

Boulikas, T., "Status of gene therapy in 1997: Molecular mechanisms, disease targets, and clinical applications" *Gene Ther. Mol. Biol.* 1:1–172 (1998).

Boulikas, T., "Nucleocytoplasmic trafficking: implications for the nuclear import of plasmid DNA during gene therapy" *Gene Ther. Mol. Biol.* 1:713–740 (1998).

Decout, A. et al., "Contribution of the hydrophobicity gradient to the secondary structure and activity of fusogenic peptides" *Mol. Membr. Biol.* 16(3):237–246 (1999).

Duguid, J.G. et al., "A physiocochemical approach for predicting the effectiveness of peptide–based gene delivery systems for use in plasmid–based gene therapy" *Biophys. J.* 74:2802–2814 (1998).

Farhood, H. et al., "Cationic liposomes for direct gene transfer in therapy of cancer and other diseases" *Ann. N.Y. Acad. Sci.* 716:23–35 (1994).

(List continued on next page.)

*Primary Examiner*—Dave T. Nguyen
(74) *Attorney, Agent, or Firm*—Antoinette F. Konski; Bingham McCutchen LLP

(57) ABSTRACT

A method for encapsulating cisplatin and other positively-charged drugs into liposomes having a different lipid composition between their inner and outer membrane bilayers is disclosed. The liposomes are able to reach primary tumors and their metastases after intravenous injection to animals and humans. The encapsulated cisplatin has a high therapeutic efficacy in eradicating a variety of solid human tumors including but not limited to breast carcinoma and prostate carcinoma. Combination of the encapsulated cisplatin with encapsulated doxorubicin or with other antineoplastic drugs are claimed to be of therapeutic value. Also of therapeutic value in cancer eradication are claimed to be combinations of encapsulated cisplatin with a number of anticancer genes including but not limited to p53, IL-2, IL-12, angiostatin, and oncostatin encapsulated into liposomes as well as combinations of encapsulated cisplatin with HSV-tk plus encapsulated ganciclovir.

26 Claims, 5 Drawing Sheets

OTHER PUBLICATIONS

Kim, J.C. et al., "Synthesis and antitumor evaluation of cis–(1,2–diaminoethane) dichloroplatinum (II) complexes linked to 5– and 6–methyleneuracil and –uridine analogues" *Arch. Pharm. Res.* 21(4):465–469 (1998).

Martin, F. and Boulikas, T., "The challenge of liposomes in gene therapy" *Gene Ther. Mol. Biol.* 1:173–214 (1998).

Martin, I. and Ruysschaert, J–M., "Comparison of lipid vesicle fusion induced by the putative fusion peptide of fertilin (a protein active in sperm–egg fusion) and the NH2—terminal domain of the HIV2 gp41" *FEBS Lett.* 405(3):351–355 (1997).

Martin, I. et al., "Membrane fusion induced by a short fusogenic peptide is assessed by its insertion and orientation into target bilayers" *Biochemistry* 38(29):9337–9347 (1999).

Morikawa, K. et al., "Synthesis of platinum complexes of 2–aminomethylpyrrolidine derivatives for use as carrier ligands and their antitumor activities" *Chem. Pharm. Bull.* (Tokyo) 38(4):930–935 (1990).

Papadopoulou, M.V. et al., "NLCQ–1, a novel hypoxic cyctoxin: Potentiation of melphalan, cisDDP and cyclophosphamide in vivo" *Int. J. Radiation Oncol. Biol. Phys.* 42(4):775–779 (1998).

Pécheur, E.I. et al., "Membrane anchorage brings about fusogenic properties in a short synthetic peptide" *Biochemistry* 36(13):3773–3781 (1997).

Stathopoulos, G.P. et al., "Paclitaxel combined with cis–platin as second–line treatment in patients with advanced non–small cell lung cancers refractory to cis–platin" *Oncol. Rep.* 6(4):797–800 (1999).

Zhang, M. et al. "Studies on Cisplatinum Albumin Microspheres for Lung Targeting" *Acta Pharmaceutica Sinica* 29 (5):380–386 English Abstract on p. 386 (1994).

Boulikas, T., "The Nonuniform Repair of Active and Inactive Chromatin Domains" *Int. J. Onco.* 8:65–75 (1996).

Boulikas, T., "A Unified Model Explaning the Preferential Repair of Active Over Inactive Genes and of the Transcribed Over the Nonstranscribed Strand: A Leading Role for Transcription Factors and Matrix Anchorage" *Int. J. Oncol.* 8:77–84 (1996).

Boulikas, T., "Nucleocytoplasmic Trafficking: Implications for the Nuclear Import of Plasmid DNA During Gene Therapy" *Gen. Ther. Mol. Biol.* 1:713–740 (1988).

Martin, F. et al., "The Challenge of Liposomes in Gene Therapy" *Gene Ther. Mol. Biol.* 1:173–214 (1988).

\* cited by examiner

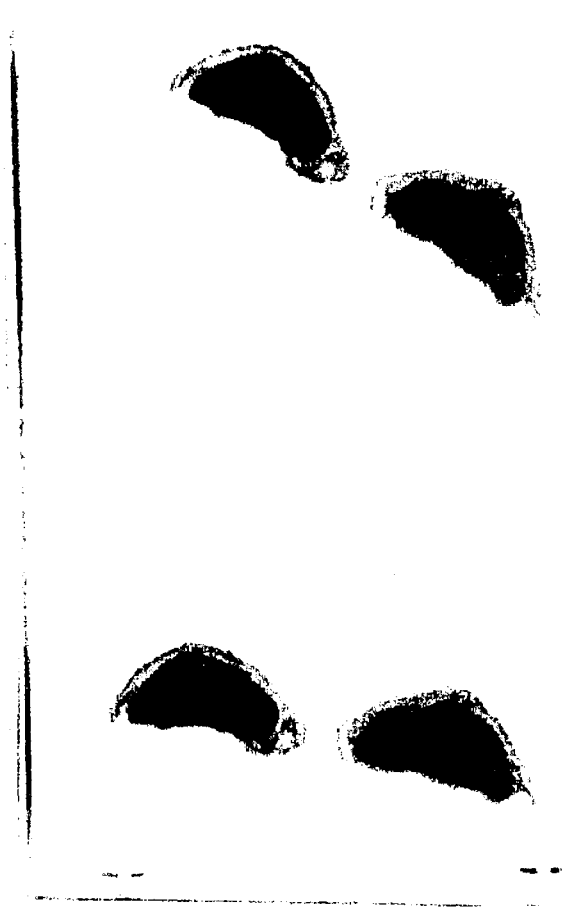
Fig. 4A            Fig. 4B

THERAPY FOR HUMAN CANCERS USING CISPLATIN AND OTHER DRUGS OR GENES ENCAPSULATED INTO LIPOSOMES

FIELD OF THE INVENTION

The present invention relates to liposome encapsulated drugs and delivery systems, specifically liposome encapsulated cisplatin. The drugs are useful to kill cancer cells in a variety of human malignancies after intravenous injection.

BACKGROUND OF THE INVENTION

Throughout this application various publications, patents and published patent specifications are referenced by author and date or by an identifying patent number. Full bibliographic citations for the publications are provided within this disclosure or immediately preceding the claims. The disclosures of these publications, patents and published patent specifications are hereby incorporated by reference into the present disclosure to more fully describe the state of the art to which this invention pertains.

Cis-diamminedichloroplatinum(II), cis-$[Pt(NH_3)_2Cl_2]^{2+}$, abbreviated cisplatin or cis-DDP, is one of the most widely used antineoplastic drugs for the treatment of testicular, ovarian carcinomas and against carcinomas of the head and neck. More than 90% of testicular cancers are cured by cisplatin. The most severe side effects are nephrotoxicity, bone marrow toxicity and gastrointestinal irritation (Oliver and Mead, 1993). Bilateral optic neuropathy was observed in a patient affected by ovarian carcinoma treated with 160 mg/$m^2$ cisplatin and 640 mg/$m^2$ carboplatin (Caraceni et al., 1997). Oral hexamethylmelamine treatment in a group of 61 patients with epithelial ovarian carcinoma with cis- or carboplatin resistance (relapse within 6 months after the end of that therapy) showed a 14% objective response rate (Vergote et al., 1992).

Cationic cholesterol derivatives have been used to deliver therapeutic agents. For example, they have been mixed with phosphatidylethanolamine and sonicated to form small unilamellar vesicles which can complex with DNA and mediate the entry into the cytosol from the endosome compartment. One of the liposome formulations, DC-Chol liposomes, has been used in a gene therapy clinical trial against melanoma. Human immunodeficiency virus-1 transactivating protein gene was codelivered with a reporter gene under the control of HIV-1 long terminal repeat. Human tumor cells selected for cisplatin resistance or isolated from patients who had failed cisplatin therapy were highly transfectable with cationic liposomes. These results suggested a serial therapy protocol with cisplatin and gene therapy for malignancy (Farhood et al., 1994).

Various platinum complexes prepared from 2-aminomethylpyrrolidine derivatives as carrier ligands were tested for their antitumor activity against Colon 26 carcinoma and P388 leukemia using subcutaneous and/or intraperitoneal injections in mice. 2-aminomethylpyrrolidine proved to be the most effective carrier ligand in its amine derivatives (Morikawa et al., 1990).

An optimum procedure was established by orthogonal test for preparing cisplatin albumin microspheres (Cis-DDP-AMS) with emulsion-heating stabilization method (mean size was 148 microns). The distribution and elimination half times of platinum were prolonged 3.36 times and 1.23 times after hepatic arterial chemoembolization with Cis-DDP-AMS versus Cis-DDP, respectively (Zhang et al., 1995).

The search for platinum (II)-based compounds with improved therapeutic properties was prompted to design and synthesize a new family of water-soluble, third generation cis-diaminedichloroplatinum (II) complexes linked to uracil and uridine. However, none of the synthesized compounds showed any significant cytotoxic activity against three cell lines that were treated (Kim et al., 1998).

The recently developed bioreductive agent 4-[3-(2-nitroimidazolyl)-propylamino]-7-chloroquinoline hydrochloride (NLCQ-1) was found to potentiate the antitumor effect of the chemotherapeutic agents melphalan (L-PAM), cisplatin (cisDDP) and cyclophosphamide (CPM) without concurrent enhancement in bone marrow toxicity. Potentiation was strictly schedule dependent and the optimum effect (1.5 to 2 logs killing beyond additivity) was observed when NLCQ-1 was given 45-min before cisDDP. These results support the classification of NLCQ-1, based on clinical studies, as a chemosensitizer (Papadopoulou et al., 1998).

A combination of paclitaxel with cisplatin as second-line treatment in patients with non-small cell lung cancer (NSCLC) who had previously undergone first-line therapy with cisplatin achieved partial response (40%) in 14 patients (Stathopoulos et al., 1999).

Abra et al. (U.S. Pat. No. 5,945,122, issued Aug. 31, 1999) describes a liposome composition containing entrapped non-charged cisplatin in mostly neutral lipids. However, the process of Abra et al. uses neutral lipids compared with the anionic lipid DPPG disclosed in the present patent for cisplatin entrapment.

Thus, while the prior reports indicate that liposome mediated delivery of cisplatin and other therapeutic drugs is possible, therapeutic efficiency has been limited by the low aqueous solubility and low stability of cisplatin. Therapeutic efficacy also is limited by the high toxicity of the drug. Thus, a need exists to reduce the difficulties involved in processing of cisplatin containing drugs and high toxicity of cisplatin when used therapeutically. This invention satisfies this need and provides related advantages as well.

DISCLOSURE OF THE INVENTION

In one aspect, this invention provides a method for encapsulating cisplatin and other positively-charged drugs into liposomes having a different lipid composition between their inner and outer membrane bilayers and able to reach primary tumors and their metastases after intravenous injection to animals and humans. In one aspect, the method includes complex formation between cisplatin with DPPG (dipalmitoyl phosphatidyl glycerol) or other lipid molecules to convert cisplatin to its aqua form by hydrolysis which is positively-charged and is the active form of cisplatin endowed with the antineoplastic activity. At this stage membrane fusion peptides and other molecules with fusogenic properties may be added to improve entrance across the cell membrane of the complex. The aqua cisplatin-DPPG micelles are converted into liposomes by mixing with vesicle forming lipids such as pre-made liposomes or lipids followed by dialysis and extrusion through membranes, entrapping and encapsulating cisplatin to a very high yield. Doxorubicin or other positively-charged compounds can be substituted for cisplatin in these formulations. The encapsulated cisplatin has a high therapeutic efficacy in eradicating a variety of solid human tumors including but not limited to breast carcinoma and prostate carcinoma. Combination of the encapsulated cisplatin with encapsulated doxorubicin or with other antineoplastic drugs are claimed to be of therapeutic value. Also of therapeutic value in cancer eradication are claimed to be combinations of encapsulated cisplatin with a number of anticancer genes including but not limited to p53, IL-2, IL-12, angiostatin, and oncostatin encapsulated into liposomes as well as combinations of encapsulated cisplatin with HSV-tk plus encapsulated ganciclovir.

BRIEF DESCRIPTION OF THE FIGURES

FIG. 3 shows histology of tumors in SCID mice with or without treatment with cisplatin.

FIG. 4 shows macroscopic (visual) difference in tumor size between an animal treated with encapsulated cisplatin (A) and an untreated animal (B)).

MODES FOR CARRYING OUT THE INVENTION

Figure 1:
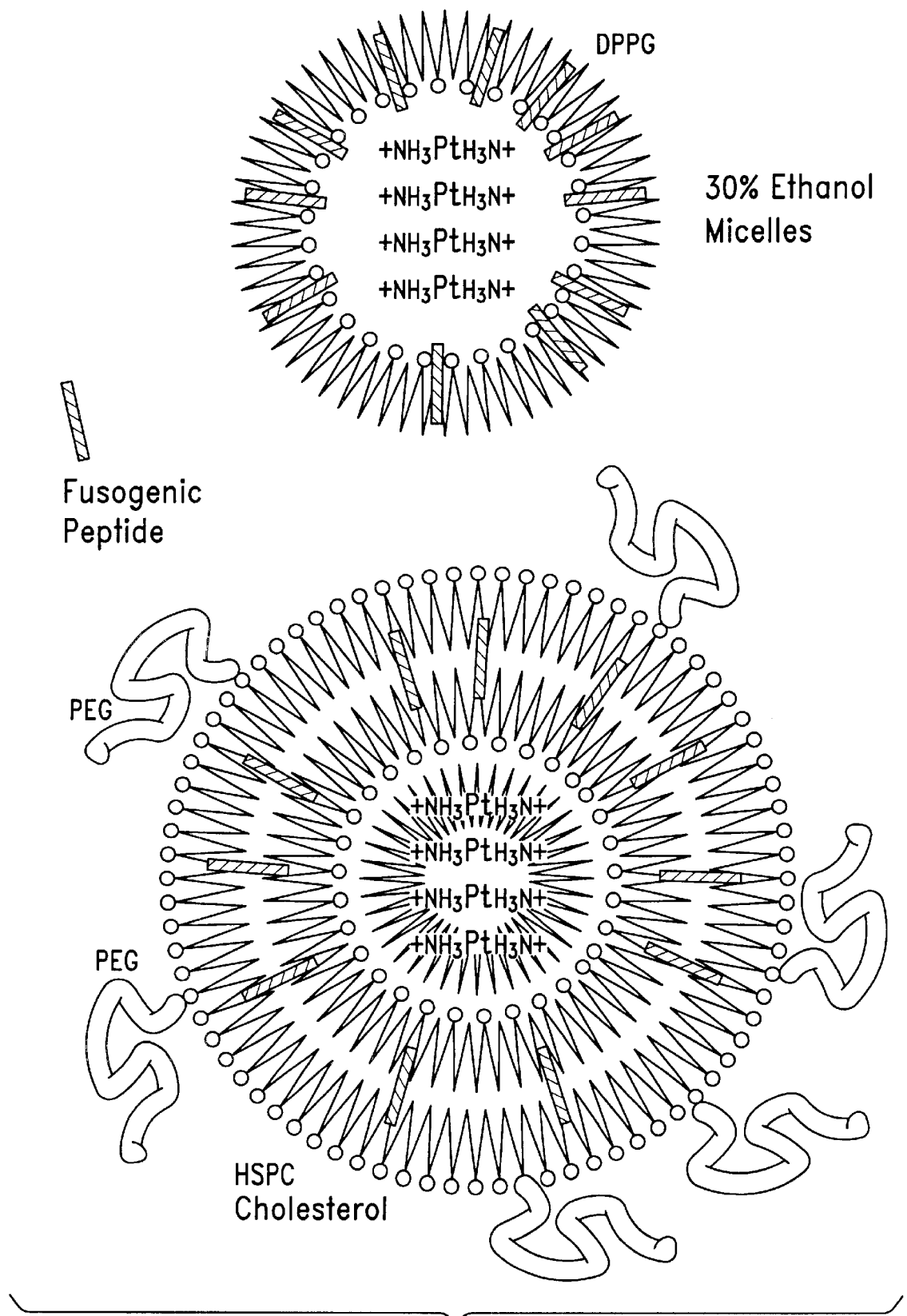
FIG. 1 depicts cisplatin encapsulation.

The practice of the present invention will employ, unless otherwise indicated, conventional techniques of immunology, molecular biology, microbiology, cell biology and recombinant DNA. These methods are described in the following publications. See, e.g., Sambrook, et al. MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.); "PCR: A PRACTICAL APPROACH" (M. MacPherson, et al., IRL Press at Oxford University Press (1991)); PCR 2: A PRACTICAL APPROACH (M. J. MacPherson, B. D. Hames and G. R. Taylor eds. (1995)); ANTIBODIES, A LABORATORY MANUAL (Harlow and Lane, eds. (1988)); and ANIMAL CELL CULTURE (R. I. Freshney, ed. (1987)).

As used in the specification and claims, the singular form "a," "an" and "the" include plural references unless the context clearly dictates otherwise. For example, the term "a cell" includes a plurality of cells, including mixtures thereof.

The term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

The terms "polynucleotide" and "nucleic acid molecule" are used interchangeably to refer to polymeric forms of nucleotides of any length. The polynucleotides may contain deoxyribonucleotides, ribonucleotides, and/or their analogs. Nucleotides may have any three-dimensional structure, and may perform any function, known or unknown. The term "polynucleotide" includes, for example, single-, double-stranded and triple helical molecules, a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A nucleic acid molecule may also comprise modified nucleic acid molecules.

A "gene" refers to a polynucleotide containing at least one open reading frame that is capable of encoding a particular polypeptide or protein after being transcribed and translated.

A "composition" is intended to mean a combination of active agent and another compound or composition, inert (for example, a detectable agent or label or a pharmaceutically acceptable carrier) or active, such as an adjuvant.

A "pharmaceutical composition" is intended to include the combination of an active agent with a carrier, inert or active, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin, REMINGTON'S PHARM. SCI., 15th Ed. (Mack Publ. Co., Easton (1975)).

An "effective amount" is an amount sufficient to effect beneficial or desired results. An effective amount can be administered in one or more administrations, applications or dosages.

A "subject," "individual" or "patient" is used interchangeably herein, which refers to a vertebrate, preferably a mammal., more preferably a human. Mammals include, but are not limited to, murines, simians, humans, farm animals, sport animals, and pets.

A "control" is an alternative subject or sample used in an experiment for comparison purpose. A control can be "positive" or "negative." For example, where the purpose of the experiment is to determine a correlation of an altered expression level of a gene with a particular type of cancer, it is generally preferable to use a positive control (a subject or a sample from a subject, carrying such alteration and exhibiting syndromes characteristic of that disease), and a negative control (a subject or a sample from a subject lacking the altered expression and clinical syndrome of that disease).

A "gene delivery vehicle" is defined as any molecule that can carry inserted polynucleotides into a host cell. Examples of gene delivery vehicles are liposomes, cationic liposomes, viruses, such as baculovirus, adenovirus, adeno-associated virus, and retrovirus, bacteriophage, cosmid, plasmid, fungal vectors and other recombination vehicles typically used in the art which have been described for expression in a variety of eukaryotic and prokaryotic hosts, and may be used for gene therapy as well as for simple protein expression.

A "viral vector" is defined as a recombinantly produced virus or viral particle that comprises a polynucleotide to be delivered into a host cell, either in vivo, ex vivo or in vitro. Examples of viral vectors include retroviral vectors, adenovirus vectors, adeno-associated virus vectors and the like.

In aspects where gene transfer is mediated by a retroviral vector, a vector construct refers to the polynucleotide comprising the retroviral genome or part thereof, and the inserted polynucleotide. As used herein, "retroviral mediated gene transfer" or "retroviral transduction" carries the same meaning and refers to the process by which a gene or nucleic acid sequences are stably transferred into the host cell by virtue of the virus entering the cell and integrating its genome into the host cell genome. The virus can enter the host cell via its normal mechanism of infection or be modified such that it binds to a different host cell surface receptor or ligand to enter the cell. As used herein, retroviral vector refers to a viral particle capable of introducing exogenous nucleic acid into a cell through a viral or viral-like entry mechanism.

Retroviruses carry their genetic information in the form of RNA; however, once the virus infects a cell, the RNA is reverse-transcribed into the DNA form, which integrates into the genomic DNA of the infected cell. The integrated DNA form is called a provirus.

In aspects where gene transfer is mediated by a DNA viral vector, such as an adenovirus (Ad) or adeno-associated virus (AAV), a vector construct refers to the polynucleotide comprising the viral genome or part thereof, and a polynucleotide to be inserted. Adenoviruses (Ads) are a relatively well characterized, homogenous group of viruses, including over 50 serotypes. (see, e.g., WO 95/27071). Ads are easy to grow and do not require integration into the host cell genome. Recombinant Ad-derived vectors, particularly those that reduce the potential for recombination and generation of wild-type virus, have also been constructed. (see, WO 95/00655; WO 95/11984). Wild-type AAV has high infectivity and specificity integrating into the host cells genome. (Hermonat and Muzyczka (1984) PNAS USA 81:6466–6470; Lebkowski, et al. (1988) Mol. Cell. Biol. 8:3988–3996).

Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

Gene delivery vehicles also include several non-viral vectors, including DNA/liposome complexes, and targeted viral protein DNA complexes. Liposomes that also comprise a targeting antibody or fragment thereof can be used in the methods of this invention. To enhance delivery to a cell, the nucleic acid or proteins of this invention can be conjugated to antibodies or binding fragments thereof which bind cell surface antigens, e.g., TCR, CD3 or CD4.

Polynucleotides are inserted into vector genomes using methods well known in the art. For example, insert and vector DNA can be contacted, under suitable conditions, with a restriction enzyme to create complementary ends on each molecule that can pair with each other and be joined together with a ligase. Alternatively, synthetic nucleic acid linkers can be ligated to the termini of restricted polynucleotide. These synthetic linkers contain nucleic acid sequences that correspond to a particular restriction site in the vector DNA. Additionally, an oligonucleotide containing a termination codon and an appropriate restriction site can be ligated for insertion into a vector containing, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColEI for proper episomal replication; versatile multiple cloning sites; stabilizing elements 3' to the inserted polynucleotide, and T7 and SP6 RNA promoters for in vitro transcription of sense and antisense RNA. Other means are well known and available in the art.

"Host cell" is intended to include any individual cell or cell culture which can be or have been recipients for vectors or the incorporation of exogenous polynucleotides, polypeptides and/or proteins. It also is intended to include progeny of a single cell, and the progeny may not necessarily be completely identical (in morphology or in genomic or total DNA complement) to the original parent cell due to natural., accidental., or deliberate mutation. The cells may be prokaryotic or eukaryotic, and include but are not limited to bacterial cells, yeast cells, plant cells, insect cells, animal cells, and mammalian cells, e.g., murine, rat, simian or human.

As used herein, the terms "neoplastic cells," "neoplasia," "tumor," "tumor cells," "cancer" and "cancer cells," (used interchangeably) refer to cells which exhibit relatively autonomous growth, so that they exhibit an aberrant growth phenotype characterized by a significant loss of control of cell proliferation (i.e., de-regulated cell division). Neoplastic cells can be malignant or benign.

"Suppressing" tumor growth indicates a growth state that is curtailed when compared to control cells. Tumor cell growth can be assessed by any means known in the art, including, but not limited to, measuring tumor size, determining whether tumor cells are proliferating using a $^3$H-thymidine incorporation assay, or counting tumor cells. "Suppressing" tumor cell growth means any or all of the following states: slowing, delaying, and stopping tumor growth, as well as tumor shrinkage.

Embodiments of the Invention

Micelles, Liposomes and Processes for Obtaining Them

Claimed herein is a new method for entrapping cisplatin into lipids which enhances the content of cisplatin per volume unit, reduces its toxicity, is able to target primary tumors and their metastases after intravenous injection, and shows shrinkage of tumors and complete therapy of SCID mice bearing human tumors.

Cisplatin is a heavy metal complex containing two chloride atoms and two amino groups in the cis position attached to one atom of the transitory heavy metal platinum in its divalent form. It is a bifunctional alkylating agent as well as DNA intercalator inhibiting DNA synthesis. In one form, cisplatin is a yellow powder of a molecular weight of 300.1 and of limited solubility of 1 mg/ml in water. It is widely used for the treatment of cancer patients, especially those of testicular, lymphomas, endometrial, bladder, ovarian, head and neck squamous cell carcinomas, breast carcinomas, and many other malignancies, often in combination with adriamycin, vinblastin, bleomycin, prednisone, vincristine, taxol, and others antineoplastic drugs as well as radiation therapy. We claim reduction in total cisplatin volume required for patient treatment because of an increase in its solubility in its lipid entrapment form The volume used for intravenous injection is usually large (about 180 ml per adult patient or about 20–120 mg/m) administered as a 24-hour infusion. It is cleared from the plasma in a rapid phase of 25–80 min followed by a slower secondary phase of 58–73 h; it is bound by plasma proteins and excreted by the kidneys (explaining the severe kidney toxicity in treated patients). Dose related nephrotoxicity can be partially overcome with vigorous hydration, mannitol, furosemide and other drugs. Other toxicities incurred by cisplatin include ototoxicity, nausea and vomiting, anemia, and mild myelosuppression (The Merck Manual of Diagnosis and Therapy). The present invention overcomes the limitations of prior art processes and compositions.

Thus, in one aspect, this invention provides methods for producing cisplatin micelles, by combining cisplatin and a phosphatidyl glycerol lipid derivative (PGL derivative) in a range of 1:1 to 1:2.1 to form a cisplatin mixture. In alternative embodiments, the range of cisplatin to PGL derivative is in the ranges 1:1.2; or 1:1.4; or 1:1.5; or 1:1.6; or 1:1.8 or 1:1.9 or 1:2.0 or 1:2.1. The mixture is then combined with an effective amount of at least a 20% organic solvent such as an ethanol solution to form cisplatin micelles.

As used herein, the term "phosphatidyl glycerol lipid derivative (PGL derivative)" is any lipid derivative having the ability to form micelles and have a net negatively charged head group. This includes but is not limited to dipalmitoyl phosphatidyl glycerol (DPPG), dimyristoyl phosphatidyl glycerol, and dicapryl phosphatidyl glycerol. In one aspect, phosphatidyl derivatives with a carbon chain of 10 to 28 carbons and having unsaturated side aliphatic side chain are within the scope of this invention. The complexation of cisplatin with negatively-charged phosphatidyl glycerol lipids having variations in the molar ratio giving the particles a net positive (1:1) neutral (1:2) or slightly negative (1:2.1 ) charge will allow targeting of different tissues in the body after administration. However, complexing of cisplatin with negatively charged PGL has been shown to enhance the solubility of cisplatin, thus reducing the volume of the drug required for effective antineoplastic therapy. In addition, the complexation of cisplatin and negatively charged PGL proceeds to very high encapsulation efficiency minimizing drug loss during the manufacturing process. These complexes are stable, do not form precipitates and retain therapeutic efficacy after storage at 4° C. for at least 4 months.

As used herein, the term "cisplatin" included analogs. Examples include carboplatin, ormaplatin, oxaplatin, 2-aminomethylpyrrolidine (1,1-cyclobutane dicarboxylato) platinum, lobaplatin, 1-cyclobutane-dicarboxylato(2-)-(2-methyl-1,4-butanediamine-N,N')platinum, zeniplatin, enloplatin, 254-S nedaplatin and JM-216 (bis-acetato-amine-dichloro-cyclohexylamine-platinum(IV)).

It is to be understood, although not always explicitly stated, that other positively charged drugs, including but not limited to the antineoplastic drug doxorubicin can be substituted for cisplatin. Alternatively, other types of drugs that are neutral can be used upon their conversion into positively charged drugs by derivation with positively charged groups. Modification of a neutral or negatively-charged anticancer or other type of drug to a positively-charged molecule can be accomplished by a number of methods well established in organic synthesis. This can be achieved for example by replacing a hydroxyl group in the drug with an amino group or by a trimethylamino group thus introducing a positive charge to the compound. Replacement of a ring hydroxyl group with an amino group is discussed in U.S. Pat. No. 5,837,868, Wang, et al. issued Nov. 17, 1998.

The above method does not require that the steps be performed in the order indicated above. For example, the method can be practiced by combining cisplatin with an effective amount of at least a 20% organic solvent solution to form a solution. The solution is combined with a phosphatidyl glycerol lipid (PGL) derivative in a range of 1:1 to 1:2.1 to form a cisplatin micelle. As above, the range of cisplatin to PGL derivative is in the ranges 1:1.2; or 1:1.4; or 1:1.5; or 1:1.6; or 1:1.8 or 1:1.9 or 1:2.0 or 1:2.1.

Any organic solvent or formulation of ethanol, or any other alcohol that does not form a two phase system, or other organic solvent (i.e., choroform), that is miscible in 20% alcohol, is useful in the methods described herein. For example, the alcohol solution can be any of at least 30%, 35%, 40%, 45% up to 90%, including any increment in between. Preferably, the alcohol solution is 30% ethanol for DPPG, and for other lipids the optimal percentage may be different.

In one embodiment, partial replacement of DPPG molecules by peptides with a net negative charge gives to cisplatin complexes having fusogenic properties able to cross the cell membrane of the target. Fusogenic peptides may also be covalently attached at the free and of PEG for their better exposure. Addition of a small amount of cationic lipids replacing positive charges of aqua cisplatin at the final cisplatin/DPPG complex also endows the complex with fusogenic properties; the percentage of positive charges to be substituted by cationic lipids (e.g., DDAB, dimethyldioctadecyl ammonium bromide; DMRIE: N-[1-(2,3-dimyristyloxy)propyl]-N,N-dimethyl-N-(2-hydroxyethyl) ammonium bromide; DMTAP: 1,2-dimyristoyl-3-trimethylammonium propane; DOGS: Dioctadecylamidoglycylspermine; DOTAP: N-(1-(2,3-dioleoyloxy)propyl)-N,N,N-trimethylammonium chloride; DPTAP: 1,2-dipalmitoyl-3-trimethylammonium propane; DSTAP: 1,2-disteroyl-3-trimethylammonium propane) is small because of the toxicity of cationic lipids. Some formulations contain an amount of the fusogenic amphiphilic lipid DOPE in the micelles.

In a further aspect, the cisplatin micelles are encapsulated into vesicle forming lipids, for example, for use in drug delivery.

The lipid encapsulated cisplatin has a high therapeutic efficacy in eradicating a variety of solid human tumors including but not limited to breast carcinoma, prostate carcinoma, glioblastoma multiform, non-small lung cell carcinoma, pancreatic carcinoma, head and neck squamous cell carcinoma and T-cell lymphomas. Accordingly in another aspect, the invention provides a method for the treatment of a variety of human malignancies using an encapsulated cisplatin or alternatively, other positively-charged antineoplastic drugs into liposomes having a different lipid composition between their inner and outer membrane bilayers. The liposome encapsulated drugs are able to reach primary tumors and their metastases after intravenous injection to animals and humans.

A combination of the encapsulated cisplatin with doxorubicin or with other antineoplastic drugs have a higher therapeutic efficacy than cisplatin alone. Also of higher therapeutic efficacy in cancer eradication are combinations of encapsulated cisplatin with a number of anticancer genes including but not limited to p53, IL-2, IL-12, angiostatin, and oncostatin encapsulated into similar type of liposomes as well as combinations of encapsulated cisplatin with HSV-tk plus encapsulated ganciclovir.

In a further aspect, the invention provides a combination of the encapsulated cisplatin with the following genes:

(i) A wild-type (wt) p53 cDNA expression vector under control of the CMV, beta-actin, or other promoters, and human origins of replication able to sustain long term expression of the p53 gene; viral origins of replication which require viral replication initiator proteins such as T antigen for their activation are nor suitable for the transfer of the p53 gene because p53 protein interacts strongly with T antigen.

(ii) A PAX5 cDNA expression vector, the only suppressor of the p53 gene known (both of the wt and mutant p53 genes) interacting with a short (10 nucleotide) regulatory region within intron 1 of the p53 gene. A major drawback in p53 gene therapy is the inactivation of the wt p53 protein by the endogenous mutated forms of p53 which are overexpressed in tumors and which are able to tetramerize with wt p53 protein; the endogenous p53 genes will be suppressed by expression of Pax5, a potent transcriptional repressor of the p53 gene. The wt p53 cDNA vector lacks intron 1 and by consequence the suppressive PAX5 binding region. It is important to suppress the endogenous mutant p53 gene expression and eliminate mutant p53 from the cancer cells to potentiate induction of apoptosis and tumor suppression.

(iii) The herpes simplex virus thymidine kinase (HSV-tk) gene. The herpes simplex virus thymidine kinase (HSV-tk) suicide gene will be also included in combinations of p53 and Pax5 genes causing interruption in DNA synthesis after ganciclovir (GCV) treatment of the animal model and human patient; this is expected to increase the strand breaks in the cancer cells and to potentiate the tumor suppressor functions of p53 known to bind to strand breaks and to damaged DNA sites. In a further embodiment, ganciclovir is combined and encapsulated into liposomes.

Gene therapy is a new era of biomedical research aimed at introducing therapeutic genes into somatic cells of patients (reviewed by Boulikas, 1998a; Martin and Boulikas, 1998). Two major obstacles prohibit successful application of somatic gene transfer: (1) the small percentage of transduced cells and (2) the loss of the transcription signal of the therapeutic gene after about 3–7 days from injection in vivo.

The first problem arises (i) from inability of delivery vehicles carrying the gene to reach the target cell surface (the vast majority of liposome-DNA complexes are eliminated from blood circulation rapidly); (ii) from difficulty to penetrate the cell membrane and (iii) to release the DNA from endosomes after internalization by cells; (iv) from inefficient import into nuclei. Others have used stealth liposomes (Martin and Boulikas, 1998a), which persist in circulation for days and concentrate in tumors. However, classical stealth liposomes are not taken up by cancer cells. Disclosed herein are strategies that are designed to enhance liposome internalization (fusogenic peptides).

The second problem results from the loss of the plasmids in the nucleus by nuclease degradation and failure to replicate autonomously leading to their dilution during cell proliferation among progeny cells or by inactivation of the foreign DNA after integration into the chromosomes of the host cell. However, the use of human sequences able to sustain extrachromosomal replication of plasmids for prolonged periods (see U.S. Patent on "Cloning method for trapping human origins of replication" by Teni Boulikas U.S. Pat. No. 5,894,060) will overcome this limitation.

Also claimed herein are tumor regression and reduction in tumor mass volume of breast, prostate and other cancers in animal models and in humans after delivery of encapsulated cisplatin (termed Lipoplatin™) or encapsulated doxorubicin, and combinations of these drugs with genes including but not limited to the p53, PAX5, and HSV-tk/ encapsulated ganciclovir, IL-2, IL-12, GM-CSF, angiostatin, IL-4, IL-7, IFN-gamma, TNF-alpha, RB, BRCA1, E1A, cytosine deaminiase in combination with encapsulated 5-fluorocytosine, bcl-2, MDR-1, p21, p16, bax, bcl-xs, E2F, IGF-I VEGF, TGF-beta genes and the like.

Accordingly, this invention also provides a method for delivering cisplatin or other therapeutic agent to a cell comprising contacting the cell with the encapsulated drugs or other intermediate, obtainable by the methods of this invention. Also provided by this invention is a method for inhibiting the growth of a tumor in a subject, comprising administering to the subject an effective amount of the encapsulated drugs obtainable by the methods of this invention. The methods can be practiced in vitro, ex vivo or in vivo.

Thus, this invention also provides combination therapy using encapsulated drugs and polynucleotides. As used herein, a polynucleotides includes but is not limited to genes encoding proteins and polypeptides as well as sequences encoding ribozymes and antisense. The combination therapy is more effective in eradicating cancer than either treatment alone because the two mechanisms are different and can achieve a synergism. For example, the property of p53 protein to bind to damaged DNA regions and free ends of DNA is known and also to trigger the mechanism of apoptosis in severely-damaged cells (reviewed by Boulikas, 1998a). Free ends of DNA in cancer cells are expected to be produced after damage by cisplatin enhancing the induction of an apoptotic pathway in these cells by the expression of the transferred wt p53 (many tumors have mutated p53 and might be unable to induce effectively this pathway). The therapeutic polynucleotide also can be inserted into a gene transfer vector prior to incorporation into the micelle.

Transfer of the wild-type p53 gene has been successfully used to slow-down tumor cell proliferation in vivo and in cell culture in numerous studies. Intratumoral injection using adenoviral/p53 vectors has been shown to be effective against lung tumors in recent clinical trials (Roth et al., 1996) and against prostate tumors on animal models (reviewed by Boulikas, 1998a). The intratumoral injection method, however, may not be applicable to metastases often associated with late stages of cancer. Systemic delivery of the p53 gene with encapsulated cisplatin and targeting of tumors in any region of the body is an effective treatment for cancer cure. We claim strategies for ameliorating or partially overcoming the four main obstacles for successful somatic gene transfer using liposomal delivery of the wt p53, pax5, HSV-tk, GM-CSF, IL-12, IL-2, IL-4, IL-7, IFN-gamma, TNF-alpha, RB, BRCA1, E1A, cytosine deaminiase in combination with encapsulated 5-fluorocytosine, bcl-2, MDR-1, p21, p16, bax, bcl-xs, E2F, IGF-I VEGF, TGF-beta, angiostatin and other genes in combination with encapsulated cisplatin and other drugs to a variety of human cancers in animal models and in patients to be tested in clinical trials. These include: (i) concentration and encapsulation of the drug and gene bullets into liposomes reducing their toxicity; (ii) targeting of solid tumors and metastases by coating of the surface of the complexes with polyethylene glycol (PEG), hyaluronic acid or other polymers; (iii) enhancement in uptake of drugs and plasmids by cancer cells because of the fusogenic peptides or small percentage of cationic lipids, and (iv) sustained expression of the genes using human origins of replication (ORIs) able to sustain episomal replication or long term expression of therapeutic genes and high levels of expression.

In a further embodiment, the polynucleotides or genes further comprise regulatory DNA sequences that sustain expression of the genes for months rather than days. This translates into fewer treatments and less suffering of the cancer patient. It can also exert a strong therapeutic effect because of higher levels of expression of the anticancer gene; the same gene placed under control of weak regulatory DNA will be ineffective.

Several experimental strategies for cancer treatment have been designed using p53 gene delivery; our novelty consists in that the endogenous mutant p53 forms, which are overexpressed in over half of human prostate malignancies especially those from advanced prostate cancer are suppressed using the PAX5 expression vector. Mutated forms of p53 have amino acid substitutions mainly in their DNA binding domain but are still able to tetramerize with the wt p53 form; p53 acts as a tetramer and the presence of high levels of endogenous mutant p53 in human cancers cells interferes with the tumor suppressor functions of the wt p53 to be delivered.

PAX5 is an homeodomain protein which determines body structures during development; PAX5 is expressed at early stages of mammalian development and in the adult during differentiation in hematopoietic stem cells; p53 gene expression is eliminated by the PAX5 suppressor protein at early stages of development allowing cells to multiply fast in the developing embryo. PAX5 is switched off at later stages throughout adulthood allowing p53 to be expressed and exert its tumor suppressive functions and to regulate apoptosis especially in the hematopoietic cell lineage.

A number of delivery systems are being used in somatic gene transfer, each associated with advantages and drawbacks. Recombinant adenoviruses do not replicate efficiently; recombinant murine retroviruses integrate randomly and are inactivated by chromatin surroundings; recombinant AAV integrates randomly and cannot achieve high titers for clinical utility. All have a maximum capacity of 3.5–7.5 kb of foreign DNA because of packaging limitations. Naked DNA is rapidly degraded (half-life 5 minutes) after systemic delivery. Cationic liposomes are toxic do not survive in circulation beyond a heart beat and target mainly the endothelium of the lung, liver, and heart. So far, only "stealth" liposomes have been proven capable of concentrating in tumor sites (also in liver and spleen) and to survive for prolonged periods in blood circulation (e.g., one day compared with minutes for non-stealth neutral liposomes and a few seconds for cationic liposomes). However, stealth liposomes are not taken readily by tumor cells remaining in the extracellular space where they release their load over days after lysis (reviewed by Martin and Boulikas, 1998); however, the aspect of the invention described below modifies stealth liposomes with fusogenic peptides or by providing a partially cationic lipid composition or DOPE at their inner bilayer which would endow them to enter the tumor cell membrane by causing disturbance of the lipid bilayer.

Having attained concentration and uptake of the drug and gene bullets in solid tumors in animals with stealth liposomes, the second step is efficacy of our drug and gene targeting approach. A human clinical trial at M. D. Anderson Cancer Center uses transfer of the wild-type p53 gene in patients suffering with non-small cell lung cancer and shown to have p53 mutations in their tumors using local injection of an Ad5/CMV/p53 recombinant adenovirus at the site of tumor in combination with cisplatin. The first results of this clinical trial are encouraging after intratumor injection of p53 (Roth et al., 1996; reviewed by Boulikas, 1998a). However, local injection is not applicable to metastases often associated with advanced stages of malignancies; in particular, prostate cancer gives metastases to bones by a mechanism involving stimulation in prostate tumor proliferation by insulin-like growth factor I (IGF-I) which is especially secreted by bone cells. Therefore, the delivery system proposed here, able to concentrate into the tumor cell mass after systemic injection, is likely to treat not only the primary tumor but also its metastases.

The proposed cisplatin liposomes will primarily target tumors because of the nature of our delivery system. The genes in the combination therapy will primarily target dividing cells because of the use of HSV-tk and ganciclovir that incorporates into replicating DNA, and primarily vascularizing tumors because of the use of stealth liposomes. Thus, liver and spleen cells that are also reached by stealth liposomes will not be killed.

In a further embodiment, the liposome encapsulated drugs described herein further comprise an effective amount of a fusogenic peptide. Fusogenic peptides belong to a class of helical amphipathic peptides characterized by a hydrophobicity gradient along the long helical axis. This hydrophobicity gradient causes the tilted insertion of the peptides in membranes, thus destabilizing the lipid core and, thereby, enhancing membrane fusion (Decout et al., 1999).

Hemagglutinin (HA) is a homotrimeric surface glycoprotein of the influenza virus. In infection, it induces membrane fusion between viral and endosomal membranes at low pH. Each monomer consists of the receptor-binding HA1 domain and the membrane-interacting HA2 domain. The NH2-terminal region of the HA2 domain (amino acids 1 to 127), the so-called "fusion peptide," inserts into the target membrane and plays a crucial role in triggering fusion between the viral and endosomal membranes. Based on substitution of eight amino acids in the region 5–14 with cysteines and spin-labeling electron paramagnetic resonance it was concluded that the peptide forms an alpha-helix tilted approximately 25 degrees from the horizontal plane of the membrane with a maximum depth of 15 angstroms (A) from the phosphate group (Macosko et al., 1997). Use of fusogenic peptides from influenza virus hemagglutinin HA-2 enhanced greatly the efficiency of transferrin-polylysine-DNA complex uptake by cells; in this case the peptide was linked to polylysine and the complex was delivered by the transferrin receptor-mediated endocytosis (reviewed by Boulikas, 1998a). This peptide had the sequence: GLFEA-IAGFIENGWEGMIDGGGYC (SEQ ID NO:1) and was able to induce the release of the fluorescent dye calcein from liposomes prepared with egg yolk phosphatidylcholine which was higher at acidic pH; this peptide was also able to increase up to 10-fold the anti-HIV potency of antisense oligonucleotides, at a concentration of 0.1–1 mM, using CEM-SS lymphocytes in culture. This peptide changes conformation at the slightly more acidic environment of the endosome destabilizing and breaking the endosomal membrane (reviewed by Boulikas, 1998a).

The presence of negatively charged lipids in the membrane is important for the manifestation of the fusogenic properties of some peptides but not of others; whereas the fusogenic action of a peptide, representing a putative fusion domain of fertilin, a sperm surface protein involved in sperm-egg fusion, was dependent upon the presence of negatively charged lipids. However, that of the HIV2 peptide was not (Martin and Ruysschaert, 1997).

For example, to analyze the two domains on the fusogenic peptides of influenza virus hemagglutinin HA, HA-chimeras were designed in which the cytoplasmic tail and/or transmembrane domain of HA was replaced with the corresponding domains of the fusogenic glycoprotein F of Sendai virus. Constructs of HA were made in which the cytoplasmic tail was replaced by peptides of human neurofibromin type 1 (NF1) (residues 1441 to 1518) or c-Raf-1, (residues 51 to 131). The constructs were expressed in CV-1 cells by using the vaccinia virus-T7 polymerase transient-expression system. Membrane fusion between CV-1 cells and bound human erythrocytes (RBCs) mediated by parental or chimeric HA proteins showed that, after the pH was lowered, a flow of the aqueous fluorophore calcein from preloaded RBCs into the cytoplasm of the protein-expressing CV-1 cells took place. This indicated that membrane fusion involves both leaflets of the lipid bilayers and leads to formation of an aqueous fusion pore (Schroth-Diez et al., 1998).

A remarkable discovery was that the TAT protein of HIV is able to cross cell membranes (Green and Loewenstein, 1988) and that a 36-amino acid domain of TAT, when chemically crosslinked to heterologous proteins, conferred the ability to transduce into cells. It is worth mentioning that the 11-amino acid fusogenic peptide of TAT (YGRKKRRQRRR (SEQ ID NO:2)) is a nucleolar localization signal (see Boulikas, 1998b).

Another protein of HIV, the glycoprotein gp41, contains fusogenic peptides. Linear peptides derived from the membrane proximal region of the gp41 ectodomain have potential applications as anti-HIV agents and inhibit infectivity by adopting a helical conformation (Judice et al., 1997). The 23 amino acid residues N-terminal peptide of HIV-1 gp41 has the capacity to destabilize negatively charged large unilamellar vesicles. In the absence of cations the main structure was a pore-forming alpha-helix, whereas in the presence of $Ca^{2+}$ the conformation switched to a fusogenic, predominantly extended beta-type structure. The fusion activity of HIV(ala) (bearing the R22(A substitution) was reduced by 70% whereas fusogenicity was completely abolished when a second substitution (V2(E) was included arguing that it is not an alpha-helical but an extended structure adopted by the HIV-1 fusion peptide that actively destabilizes cholesterol-containing, electrically neutral membranes (Pereira et al., 1997).

The prion protein (PrP) is a glycoprotein of unknown function normally found at the surface of neurons and of glial cells. It is involved in diseases such as bovine spongiform encephalopathy, and Creutzfeldt-Jakob disease in the human, where PrP is converted into an altered form (termed PrPSc). According to computer modeling calculations, the 120 to 133 and 118 to 135 domains of PrP are tilted lipid-associating peptides inserting in a oblique way into a lipid bilayer and able to interact with liposomes to induce leakage of encapsulated calcein (Pillot et al., 1997b).

The C-terminal fragments of the Alzheimer amyloid peptide (amino acids 29–40 and 29–42) have properties related to those of the fusion peptides of viral proteins inducing fusion of liposomes in vitro. These properties could mediate a direct interaction of the amyloid peptide with cell membranes and account for part of the cytotoxicity of the amyloid peptide. In view of the epidemiologic and biochemical linkages between the pathology of Alzheimer's disease and apolipoprotein E (apoE) polymorphism, examination of the potential interaction between the three common apoE isoforms and the C-terminal fragments of the amyloid peptide showed that only apoE2 and apoE3, not apoE4, are potent inhibitors of the amyloid peptide fusogenic and aggregational properties. The protective effect of apoE against the formation of amyloid aggregates was thought to be mediated by the formation of stable apoE/amyloid peptide complexes (Pillot et al., 1997a; Lins et al., 1999).

The fusogenic properties of an amphipathic net-negative peptide (WAE 11), consisting of 11 amino acid residues were strongly promoted when the peptide was anchored to a liposomal membrane; the fusion activity of the peptide appeared to be independent of pH and membrane merging and the target membranes required a positive charge which was provided by incorporating lysine-coupled phosphatidylethanolamine (PE-K). Whereas the coupled peptide could cause vesicle aggregation via nonspecific electrostatic interaction with PE-K, the free peptide failed to induce aggregation of PE-K vesicles (Pecheur et al., 1997).

A number of studies suggest that stabilization of an alpha-helical secondary structure of the peptide after insertion in lipid bilayers in membranes of cells or liposomes is responsible for the membrane fusion properties of peptides; $Zn^{2+}$, enhances the fusogenic activity of peptides because it stabilizes the alpha-helical structure. For example, the HEXXH domain of the salivary antimicrobial peptide, located in the C-terminal functional domain of histatin-5, a recognized zinc-binding motif is in a helicoidal conformation (Martin et al., 1999; Melino et al., 1999; Curtain et al., 1999).

Fusion peptides have been formulated with DNA plasmids to create peptide-based gene delivery systems. A combination of the YKAKnWK peptide, used to condense plasmids into 40 to 200 nm nanoparticles, with the GLFEALLELLESLWELLLEA (SEQ ID NO:3) amphipathic peptide, which is a pH-sensitive lytic agent designed to facilitate release of the plasmid from endosomes enhanced expression systems containing the beta-galactosidase reporter gene (Duguid et al., 1998).

DOPE (dioleyl phosphatidyl ethanolamine) is a fusogenic lipid; elastase cleavage of N-methoxy-succinyl-Ala-Ala-Pro-Val-DOPE (SEQ ID NO:10) converted this derivative to DOPE (overal positive charge) to deliver an encapsulated fluorescent probe, calcein, into the cell cytoplasm (Pak et al., 1999). An oligodeoxynucleic sequence of 30 bases complementary to a region of beta-endorphin mRNA elicited a concentration-dependent inhibition of beta-endorphin production in cell culture after it was encapsulated within small unilamellar vesicles (50 nm) containing dipalmitoyl-DL-alpha-phosphatidyl-L-serine endowed with fusogenic properties (Fresta et al., 1998).

Additional fusogenic peptides (SEQ ID NOS:4 through 9) useful in the methods of this invention are described in Table 1, below.

| Fusogenic peptide | Source Protein | Properties | Reference |
| --- | --- | --- | --- |
| GLFEAIAGFIENG WEGMIDGGGYC | Influenza virus hemagglutinin HA-2 | | Bongartz et al, 1994; |
| YGRKKRRQRRR | TAT of HIV | | Green and Loewenstein, 1988; |
| the 23-residue fusogenic N-terminal peptide | HIV-1 transmembrane glycoprotein gp41 | Was able of inserting as an alpha-helix into neutral phospholipid bilayers | Curtain et al, 1999 |
| 120 to 133 and 118 to 135 domains | prion protein | tilted lipid-associating peptide; interact with liposomes to induce leakage of encapsulated calcein | Pillot et al, 1997b |
| 29–42-residue fragment | Alzheimer's bcia-amyloid peptide | Endowed with capacities resembling those | Lins et al, 1999 |

-continued

| Fusogenic peptide | Source Protein | Properties | Reference |
|---|---|---|---|
| nonaggregated amyloid beta-peptide (1–40) | Alzheimer's beta-amyloid peptide | of the tilted fragment of viral fusion proteins induces apoptotic neuronal cell death | Pillot et al, 1999 |
| LCAT 56–68 helical segment | lecithin cholesterol acyltransferase (LCAT) | forms stable beta-sheets in lipids | Peelman et al, 1999; Decout et al, 1999 |
| 70 residue peptide (SV-t117) | Fusion peptide and N-terminal heptad repeat of Sendai virus | Induced lipid mixing of egg phosphatidylcholine/phosphatidylglycerol (PC/PG) large unilamellar vesicles (LUVs) | Ghosh and Shai, 1999 |
| MSGTFGGILAGL IGLL | N-terminal region of the S protein of duck hepatitis B Virus (DHBV) | Was inserted into the hydrophobic core of the lipid bilayer and induced leakage of internal aqueous contents from both neutral and negatively charged liposomes | Rodriguez-Crespo et al, 1999 |
| MSPSSLLGLLAG LQVV | S protein of woodchuck hepatitis B virus (WHV) | Was inserted into the hydrophobic core of the lipid bilayer and induced leakage of internal aqueous contents from both neutral and negatively charged liposomes | Rodriguez-Crespo et al, 1999 |
| peptide sequence B18 | membrane-associated sea urchin sperm protein bindin | Triggers fusion between lipid vesicles; a histidine-rich motif for binding zinc, is required for the fusogenic function | Ulrich et al, 1999 |
| | histatin-5 (salivary antimicrobial peptide) | Aggregates and fuses negatively charged small unilamellar vesicles in the presence of $Zn^{2+}$ | Melino et al, 1999 |
| amphipathic negatively charged peptide consisting of 11 residues (WAE) | | Forms an alpha-helix inserted and anchored into the membrane (favored at 37° C.) oriented almost parallel to the lipid acyl chains; promotes fusion of large unilamellar liposomes (LUV) | Martin et al, 1999 |
| A polymer of polylysine (average 190) partially substituted with histidyl residues | | histidyl residues become cationic upon protonation of the imidazole groups at pH below 6.0.; disrupt endosomal membranes | Midoux and Monsigny, 1999 |
| GLFEALLELLESL WELLLEA | | amphipathic peptide; a pH-sensitive lytic agent to facilitate release of the plasmid from endosomes | Duguid et al, 1998 |
| $(LKKL)_4$ | | amphiphilic fusogenic peptide, able to interact | Gupta and Kothekar, 1997 |
| residues 53–70 (C-terminal helix) | apolipoprotein (apo) AII | with four molecules of DMPC induces fusion of unilamellar lipid vesicles and displaces apo AI from HDL and r-HDL | Lambert et al, 1998 |
| residues 90–111 | PH-30 alpha (a protein functioning in sperm-egg fusion) | membrane-fusogenic activity to acidic phospholipid bilayers | Niidome et al, 1997 |
| N-terminus of Nef | Nef protein of human immunodeficiency type 1 (HIV-1) | membrane-perturbing and fusogenic activities in artificial membranes; causes cell killing in E. coli and yeast | Macreadie et al, 1997 |
| casein signal peptides | alpha s2- and beta-casein | Interact with dimyristoylphosphatidylglycerol and -choline liposomes; show both lytic and fusogenic activities | Creuzenet et al, 1997 |
| amino-terminal sequence F1 polypeptide | F1 polypeptide of measles virus (MV) | Can be used as a carrier system for CTL epitopes | Partidos et al, 1996 |
| 23 hydrophobic amino acids in the amino-terminal region | S protein of hepatitis B virus (HBV) | A high degree of similarity with known fusogenic peptides from other viruses. | Rodriguez-Crespo et al, 1994 |
| 19–27 amino acid segment | glycoprotein gp51 of bovine leukemia virus | Adopts an amphiphilic structure and plays a key role in the fusion events induced by bovine leukemia virus | Voneche et al, 1992 |
| Ac-(Leu-Ala-Arg-Leu)$_3$-NHCH$_3$ | basic amphipathic peptides | caused a leakage of contents from small unilamellar vesicles composed of egg yolk phosphatidylcholine and egg yolk phosphatidic acid (3:1) | Suenaga et al, 1989; Lee et al, 1992 |
| amphiphilic anionic peptides $E_5$ and $E_5L$ | | can mimic the fusogenic activity of influenza hemagglutinin(HA) | Murata et al, 1991 |
| 30-amino acid peptide with the major repeat unit Glu-Ala-Leu-Ala (GALA)$_7$ | designed to mimic the behavior of the fusogenic sequences of viral fusion proteins | becomes an amphipathic alpha-helix as the pH is lowered to 5.0; fusion of phosphatidylcholine small unilamellar vesicles induced by GALA requires a peptide length greater than 16 amino acids | Parente et al, 1988 |
| pardaxin | amphipathic polypeptide, purified from the gland secretion of the Red Sea Moses sole flatfish Pardachirus marmoratus | forms voltage-gated, cation-selective pores; mediated the aggregation of liposomes composed of phosphatidylserine but not of phosphatidylcholine | Lelkes and Lazarovici, 1988 |
| Gramicidin (linear hydrophobic polypeptide) | | Antibiotic; induces aggregation and fusion of vesicles | Massari and Colonna, 1986; Tournois et |

-continued

| Fusogenic peptide | Source Protein | Properties | Reference |
|---|---|---|---|
| poly(Glu-Aib-Leu-Aib) (Aib represents 2-aminoisobutyric acid), | | Amphiphilic structure upon the formation of alpha-helix; caused fusion of EYPC liposomes and dipalmitoyl-phosphatidylcholine liposomes more strongly with decreasing pH | al, 1990 Kono et al, 1993 |

After the micelles have been formed, they are mixed with an effective amount of a vesicle forming lipid to form drug containing liposomes. Useful lipids for this invention include premade neutral liposomes, lipids in powder, PEG-DSPE or hydrogenated soy phosphatidylchline (HSPC). Vesicle-forming lipids are selected to achieve a specified degree of fluidity or rigidity of the final complex providing the lipid composition of the outer layer. These can be composed of 10–60% cholesterol and the remaining amounts include bipolar phospholipids, such as the phosphatidylcholine (PC) or phosphatidylethanolamine (PE), with a hydrocarbon chain length in the range of 14–22, and saturated with one or more double C=C bonds. A preferred lipid for use in the present invention is cholesterol (10–60%), hydrogenated soy phosphatidylcholine (HSPC) at 40–90%, and the derivatized vesicle-forming lipid PEG-DSPE at 1–7%. The liposomes provide the outer lipid bilayer surfaces that are coated with the hydrophilic polymer, PEG. The PEG chains have a molecular weight between 1,000–5,000 Dalton. Other hydrophilic polymers include hyaluronic acid, polyvinylpyrrolidone, DSPE, hydroxyethylcellulose, and polyaspartamide. PEG-DSPC and PEG-HSPC are commercially available from Syngena.

Prior to mixture with the vesicle forming lipid, the ethanol or other organic solvent can be removed by any method known in the art, e.g., dialysis of the micelles through permeable membranes.

Diagnostic and Therapeutic Methods

We claim the therapy of subject, e.g., mammals such as mice, rats, simians, and human patients, with human cancers including, but not limited to breast, prostate, colon, non-small lung, pancreatic, testicular, ovarian, cervical carcinomas, head and neck squamous cell carcinomas. In one aspect, intravenous injection of cisplatin encapsulated into liposomes as well as by combinations of encapsulated cisplatin with encapsulated doxorubicin, fluorodeoxyuridine, bleomycin, adriamycin, vinblastin, prednisone, vincristine, taxol or radiation therapy, encapsulated oligonucleotides, ribozymes endowed with anticancer properties and a number of anticancer genes including but not limited to p53/Pax5/HSV-tk genes, are claimed. Our approach consists of two major parts: (i) the ability to target cancer cells (ii) effectiveness of our approach to kill cancer cells.

Accordingly, this invention also provides a method for delivering cisplatin or other therapeutic agent to a cell comprising contacting the cell with the encapsulated drugs obtainable by the methods of this invention. Also provided by this invention is a method for inhibiting the growth of a tumor in a subject, comprising administering to the subject an effective amount of the encapsulated drugs obtainable by the methods of this invention. Depending on the composition of the lipid/micelle formulation, also claimed herein are methods for targeting solid tumors and metastases in a subject by intravenous administration of an effective amount of the encapsulated drug and methods for penetrating the cell membrane of a tumor in a subject by administration of an effective amount of the encapsulated drug, wherein the micelle contains a free fusogenic peptide or a fusogenic peptide-lipid conjugate.

The methods can be practiced in vitro, ex vivo or in vitro. In vitro practice of the method involves removal of a tumor biopsy or culturing of a cell sample containing tumor cells. The final liposome complex or any intermediate product arising during cisplatin encapsulation (e.g., micelles shown in FIG. 1A) are contacted with the cell culture under conditions suitable for incorporation of the drug intracellularly. The in vitro method is useful as a screen to determine the best drug therapy for each individual patient. Inhibition of cell growth or proliferation indicates that the cell or tumor is suitably treated by this therapy. Effective amount of drug for each therapy varies with the tumor being treated and the subject being treated. Effective amounts can be empirically determined by those of skill in the art.

When delivered to an animal, the method is useful to further confirm efficacy of the drug or therapy for each tumor type. As an example of suitable animal models, groups of SCID mice or nude mice (Balb/c NCR nu/nu female, Simonsen, Gilroy, Calif.) may be subcutaneously inoculated with about $10^5$ to about $10^9$ cancer or target cells as defined herein. When the tumor is established, the liposome is administered.

As used herein, "administration, delivered or administered" is intended to include any method which ultimately provides the drug/liposome complex to the tumor mass. Examples include, but are not limited to, topical application, intravenous administration, parenteral administration or by subcutaneous injection around the tumor. Tumor measurements to determine reduction of tumor size are made in two dimensions using venier calipers twice a week.

For in vivo administration, the pharmaceutical compositions are preferably administered parenterally, i.e., intravenously, intraperitoneally, subcutaneously, intrathecally, injection to the spinal cord, intramuscularly, intraarticularly, portal vein injection, or intratumorally. More preferably, the pharmaceutical compositions are administered intravenously or intratumorally by a bolus injection. In other methods, the pharmaceutical preparations may be contacted with the target tissue by direct application of the preparation to the tissue. The application may be made by topical, "open" or "closed" procedures. By "topical", it is meant the direct application of the pharmaceutical preparation to a tissue exposed to the environment, such as the skin, nasopharynx, external auditory canal, eye, inhalation to the lung, genital mucosa and the like. "Open" procedures are those procedures which include incising the skin of a patient and directly visualizing the underlying tissue to which the pharmaceutical preparations are applied. This is generally accomplished by a surgical procedure, such as a thoracotomy to access the lungs, abdominal laparotomy to access abdominal viscera, or other direct surgical approach to the target tissue. "Closed" procedures are invasive procedures in which the internal target tissues are not directly visualized, but accessed via inserting instruments through small wounds in the skin. For example, the preparations may be administered to the peritoneum by needle lavage. Likewise, the pharmaceutical preparations may be administered to the meninges or spinal cord by infusion during a lumbar puncture followed by appropriate positioning of the patient as commonly practiced for spinal anesthesia or metrazamide imaging of the spinal cord. Alternatively, the preparations may be administered through endoscopic devices.

Administration in vivo can be effected in one dose, continuously or intermittently throughout the course of treatment. Methods of determining the most effective means and dosage of administration are well known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents can be empirically determined by those of skill in the art.

The agents and compositions of the present invention can be used in the manufacture of medicaments and for the treatment of humans and other animals by administration in accordance with conventional procedures, such as an active ingredient in pharmaceutical compositions.

Ideally, the drug/lipid formulation should be administered to achieve peak concentrations of the active compound at sites of disease. This may be achieved, for example, by the intravenous injection of the drug/lipid formula. Desirable blood levels of the drug may be maintained by a continuous infusion to provide a therapeutic amount of the active ingredient within disease tissue. The use of operative combinations is contemplated to provide therapeutic combinations requiring a lower total dosage of each component drugs than may be required when each individual therapeutic compound or drug is used alone, thereby reducing adverse effects.

While it is possible for the drug/lipid formula to be administered alone, it is preferable to present it as a pharmaceutical formulation comprising at least one active ingredient, as defined above, together with one or more pharmaceutically acceptable carriers therefor and optionally other therapeutic agents. Each carrier must be "acceptable" in the sense of being compatible with the other ingredients of the formulation and not injurious to the patient.

Designing the third generation of vehicles for the delivery of anticancer drugs and genes to solid tumors at as described herein was the result of five major improvements over existing technologies:

1.) Encapsulation of antineoplastic drugs into sterically stabilized liposomes has reduced manifold their toxicity. This is anticipated to bring to an end the nightmare of cancer patients subject to chemotherapy. Most antineoplastic drugs under current use have severe side effects such as hair loss, vomiting, weight loss and cause infarction as well as damage to kidneys, brain, liver and all other vital tissues. The antineoplastic drugs described herein are hidden inside the lumen of the lipid bilayer, are not visible to most tissues and concentrate into their tumor targets, not in every tissue in the body. Upon their uptake by the solid tumor they exert a specific cytotoxic effect to cancer cells without damaging normal cells.

2.) Targeting of solid tumors and their metastases all over the body. Over 95% of cancer patients succumb from complications connected to metastases, not from the primary tumor. Our gene and drug delivery system hag been designed to evade the immune system after intravenous administration of the gene and drug bullet reaching not only the primary tumor but also every metastasis in the animal and human body regardless of the size of the tumor. It is based on the long circulation time of our drug and gene carrying vehicles and their extravasation through the vascular endothelium of tumors because of its imperfections and leakiness at its initial stage of formation (neoangiogenesis in growing tumors) as well as because of differences in hydrostatic pressure between the growing solid tumor and normal body tissues. The liposomes of this invention have a different composition between their inner and outer lipid layers permitting efficient encapsulation and tumor targeting.

3.) Uptake of the liposome bullet by the cancer cell. The liposome bullets are able to promote fusion with the cell membrane. Similar "stealth" bullets developed elsewhere are unable to cross the membrane barrier of the cancer cell.

4.) Reaching nearly 100% liposome encapsulation efficiency for anticancer drugs, oligonucleotides and genes is a major advancement. This means minimal loss and cost effective use of drugs and genes. It also translated into simpler steps in manufacturing the anticancer bullet.

5.) The unique technology described herein can identify regulatory DNA sequences that sustain expression of the genes in the anticancer bullet for months rather than days. This translates into fewer treatments and less suffering of the cancer patient. It can also exert a strong therapeutic effect because of higher levels of expression of the anticancer gene; the same gene placed under control of weak regulatory DNA will be ineffective.

The following examples are intended to illustrate, and not limit the invention.

EXAMPLES

Preparation of Micelles and Lipid-Encapsulated Cisplatin

One formula for encapsulation includes the steps of: (A) mixing cisplatin (in powder or other form) with DPPG (dipalmitoyl phosphatidyl glycerol) or other negatively-charged lipid molecules at a 1:1 to 1:2 molar ratio in at least a 30% ethanol, 0.1 M Tris HCl, pH 7.5 to achieve about 5 mg/ml final cisplatin concentration. Variations in the molar ratio between cisplatin and DPPG are also of therapeutic value targeting different tissues. (B) Heating at 50° C. During steps A and B the initial powder suspension, which tends to give a precipitate of the yellow cisplatin powder, is converted into a gel (colloidal) form; during steps A and B there is conversion of cisplatin to its aqua form (by hydrolysis of the chloride atoms and their replacement by water molecules bound to the platin) which is positively-charged and is the active form of cisplatin endowed with the antineoplastic activity; the aqua cisplatin is simultaneously complexed with the negatively-charged lipid into micelles in 30% ethanol. This cisplatin-DPPG electrostatic complex has already improved properties over free cisplatin in tumor eradication. (C) The properties of the complex (and of the final formulation after step D, see below) in passing through the tumor cell membrane after reaching its target are improved by addition of peptides and other molecules that give to the complex this property. (D) The cisplatin-DPPG micelle complex is converted into liposomes encapsulating the cisplatin-DPPG monolayer (FIG. 1 top) or to other type of complexes by direct addition of premade liposomes followed by dialysis against saline and extrusion through membranes to downsize these to 100–160 nm in diameter (FIG. 1 bottom). It is the lipid composition of added liposomes that determines the composition of the outer surface of our final cisplatin formulation.

Variations in step (A) permit encapsulation of doxorubicin and other positively charged antineoplastic compounds. Addition of positively charged groups to neutral or negatively-charged compounds allows their encapsulation similarly into liposomes.

Therapeutic Application

Figure 2:
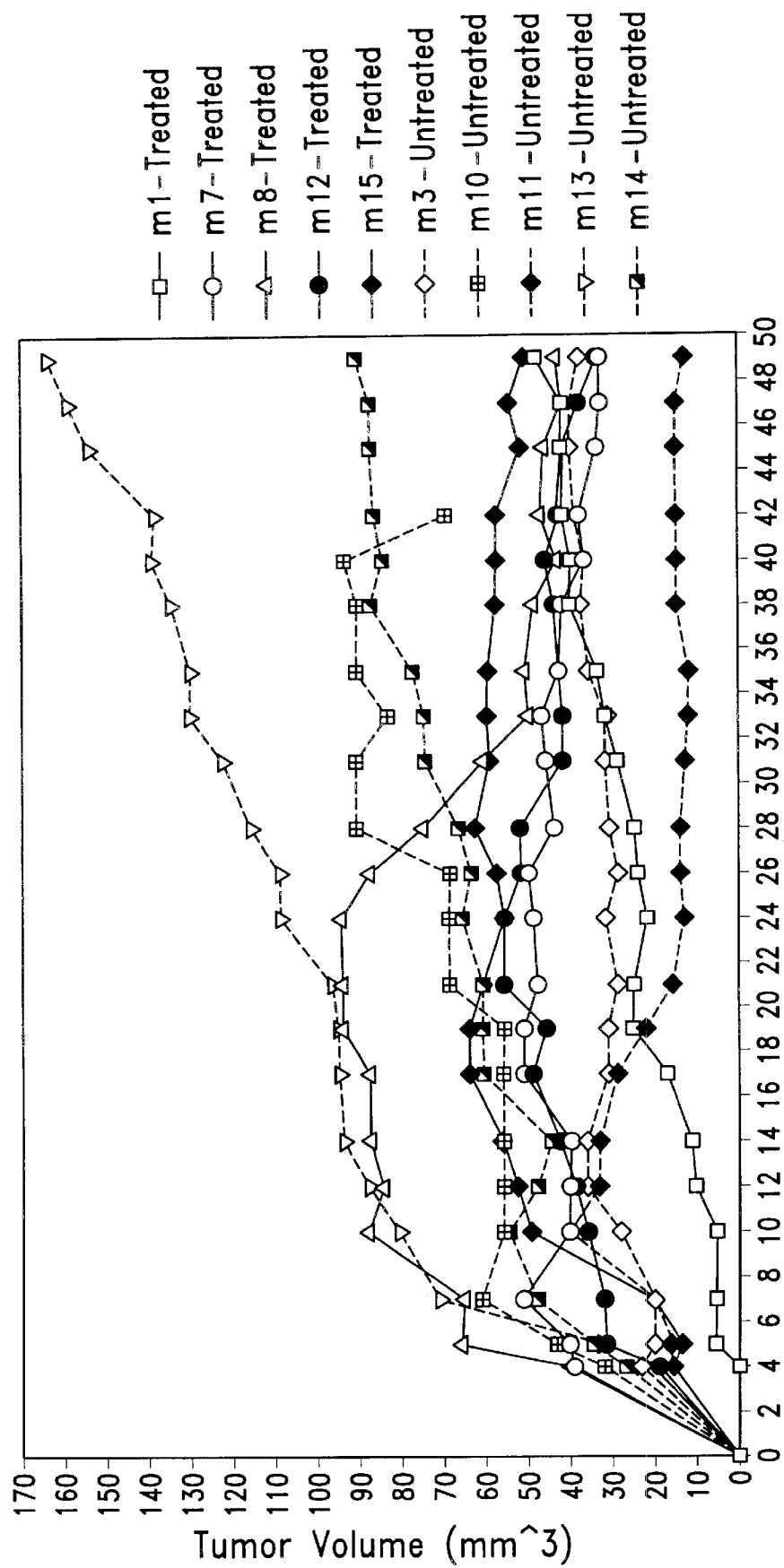
FIG. 2 shows MCF-7 tumor regression in SCID mice after 3–4 injections of encapsulated cisplatin.
Figure 3A:
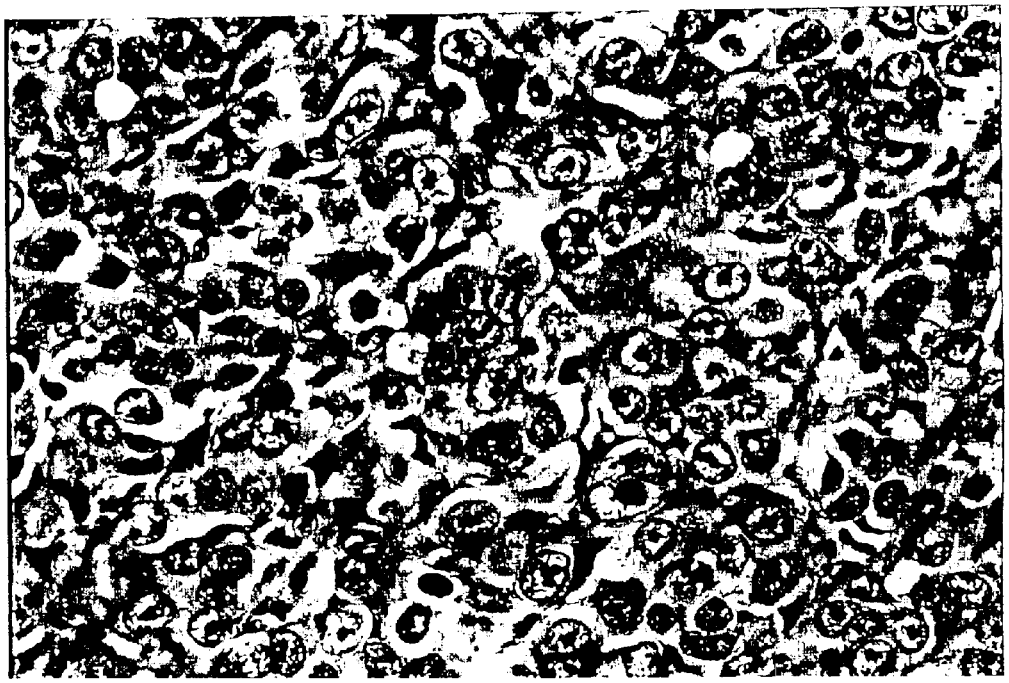
FIG. 3A shows untreated MCF-7 tumors grown in SCID mice. 40× magnification. Notice the homogeneous pattern of structures characteristic of tumor tissue.
Figure 3B:
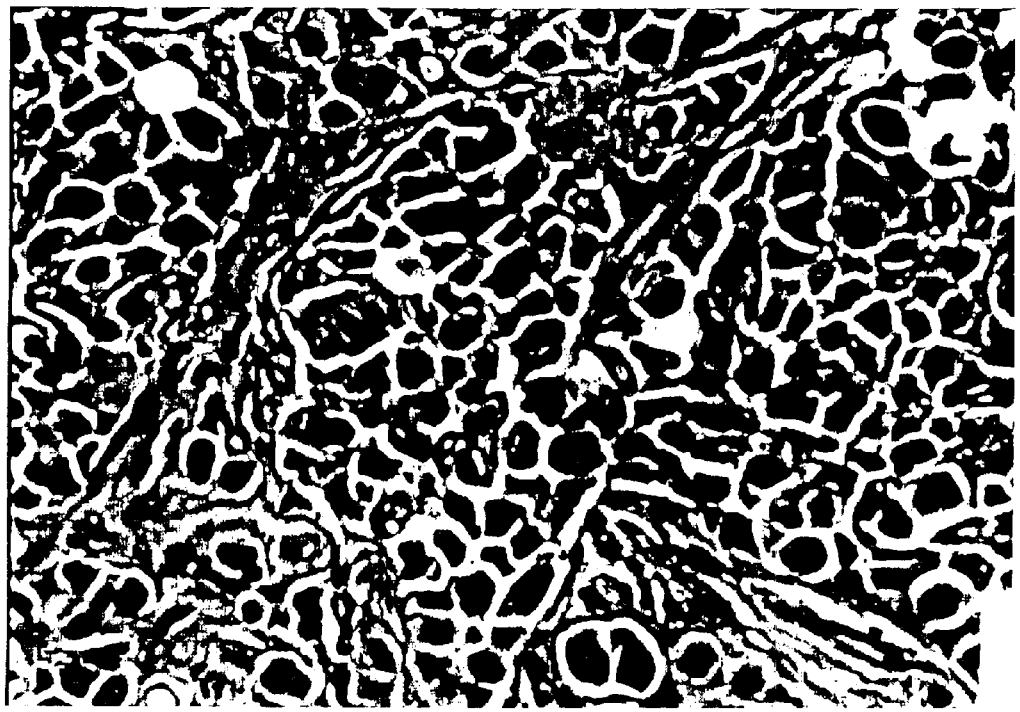
FIG. 3B shows cisplatin-treated mice (4 injections). Cells are apoptotic, there are groups of cells into structures and nuclei stain bigger and darker, characteristic of apoptotic cells.
Figure 3C:
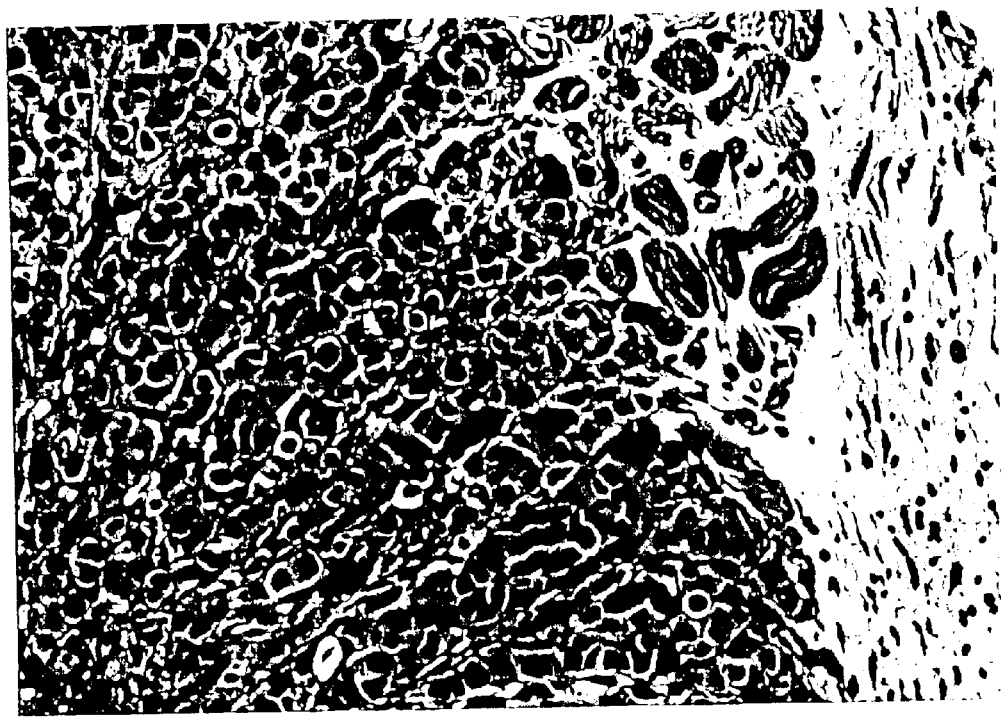
FIG. 3C shows tumors from untreated animals showing invasion to muscle. 20×.
Figure 3D:
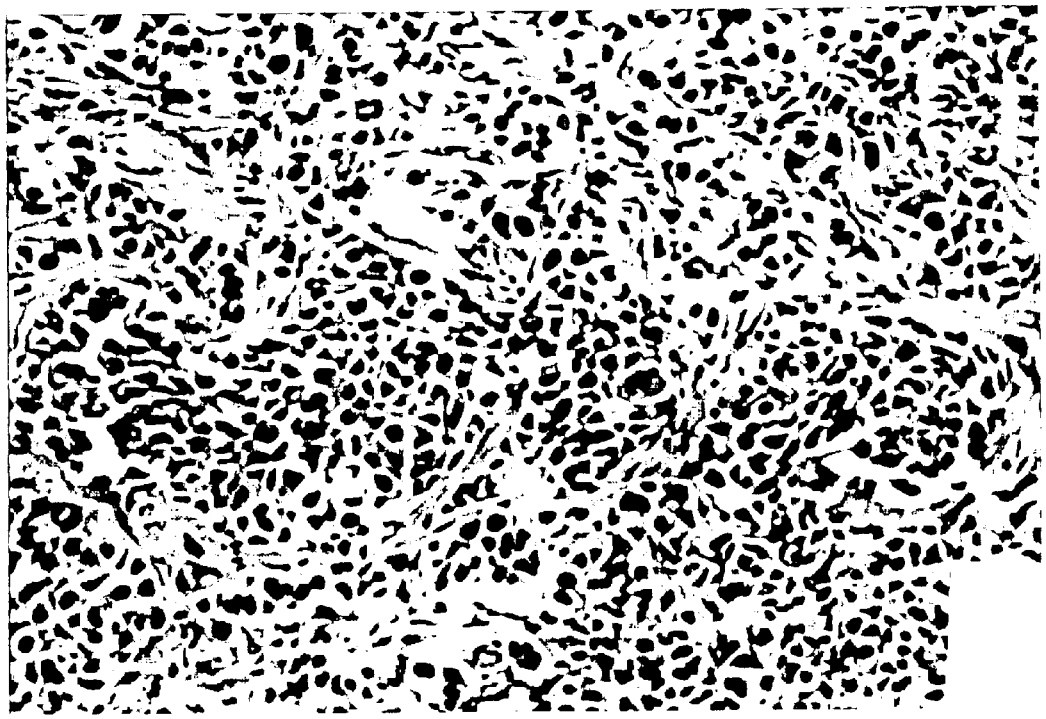
FIG. 3D shows cisplatin-treated mice. Invasion is not evident. 20× magnification.

Ninety (90) day-release estrogen pellets were implanted subcutaneously into SCID female mice. The mice were subcutaneously injected at mammary fat pad with 7.5 million MCF-7 (a human breast carcinoma available from the ATCC) cells in 0.1 ml PBS. After establishment of tumors, the mice were injected intravenously at tail vein with 0.1 ml of cisplatin liposomes. Results are shown in FIGS. 2 to 4.

While the invention has been described in detail and with reference to specific embodiments thereof, it will be apparent to one skilled in the art that various changes and modifications can be made therein without departing from the spirit and scope thereof.

REFERENCES

Ban M, Hettich D, Huguet N (1994) Nephrotoxicity mechanism of cis-platinum (II) diamine dichloride in mice. Toxicol Lett, 71(2):161–8

Bellon S F, Coleman J H and Lippard S J (1991) DNA Unwinding Produced by Site-Specific Intrastrand Cross-Links of the Antitumor Drug cis-Diamminedichloroplatinum(II). Biochemistry 30, 8026–8035.

Bongartz J-P, Aubertin A-M, Milhaud P G, and Lebleu B (1994) Improved biological activity of antisense oligonucleotides conjugated to a fusogenic peptide. Nucleic Acids Res 22, 4681–4688.

Boulikas T (1992) Evolutionary consequences of preferential damage and repair of chromatin domains. J. Mol. Evol. 35, 156–180.

Boulikas, T (1996a) The nonuniform repair of active and inactive chromatin domains. Int J Oncol 8, 65–75.

Boulikas T (1996b) A unified model explaining the preferential repair of active over inactive genes and of the transcribed over the nontranscribed strand: a leading role for transcription factors and matrix anchorage. Int J Oncol 8, 77–84.

Boulikas T (1996c) DNA lesion-recognizing proteins and the p53 connection. Anticancer Res 16, 225–242.

Boulikas T (1998a) Status of gene therapy in 1997: molecular mechanisms, disease targets, and clinical applications. Gene Ther Mol Biol 1, 1–172.

Boulikas T (1998b) Nucleocytoplasmic trafficking: implications for the nuclear import of plasmid DNA during gene therapy. Gene Ther Mol Biol 1, 713–740.

Brown S J, Kellett P J and Lippard S J (1993) lxr1, a Yeast Protein That Binds to Platinated DNA and Confers Sensitivity to Cisplatin. Science 261, 603–605.

Bruhn S L, Pil P M, Essigman J M, Housman D E, and Lippard S J (1992) Isolation and characterization of human cDNA clones encoding a high mobility group box protein that recognizes structural distortions to DNA caused by binding of the anticancer agent cisplatin. Proc Natl Acad Sci USA 89, 2307–2311.

Buchanan R L and Gralla J D (1990) Cisplatin Resistance and Mechanism in a Viral Test System: SV40 Isolates That Resist Inhibition by the Antitumor Drug Have Lost Regulatory DNA. Biochemistry 29, 3436–3442.

Caraceni A, Martini C, Spatti G, Thomas A, Onofrj M (1997) Recovering optic neuritis during systemic cis-platin and carboplatin chemotherapy. Acta Neurol Scand, 96(4):260–1

Chao C C-K, Huang S-L and Lin-Chao S (1991) $Ca^{2+}$-mediated inhibition of a nuclear protein that recognizes UV-damaged DNA and is constitutively overexpressed in resistant human cells: DNA-binding assay. Nucleic Acids Res. 19, 6413–6418.

Chu G and Chang E (1988) Xeroderma Pigmentosum Group E Cells Lack a Nuclear Factor That Binds to Damaged DNA. Science 242, 564–567.

Chu G and Chang E (1990) Cisplatin-resistant cells express increased levels of a factor that recognizes damaged DNA. Proc Natl Acad Sci USA 87, 3324–3327.

Clugston C K, McLaughlin K, Kenny M K and Brown R (1992) Binding of Human Single-Stranded DNA Binding Protein to DNA Damaged by the Anticancer Drug cis-Diamminedichloroplatinum (II). Cancer Res 52, 6375–6379.

Creuzenet C, Durand C, Haertle T (1997) Interaction of alpha s2- and beta-casein signal peptides with DMPC and DMPG liposomes. Peptides, 18(4):463–72

Curtain C, Separovic F, Nielsen K, Craik D, Zhong Y, Kirkpatrick A (1999) The interactions of the N-terminal fusogenic peptide of HIV-1 gp41 with neutral phospholipids. Eur Biophys J, 28(5):427–36

Decout A, Labeur C, Vanloo B, Goethals M, Vandekerckhove J, Brasseur R, Rosseneu M (1999) Contribution of the hydrophobicity gradient to the secondary structure and activity of fusogenic peptides. Mol Membr Biol, 16(3):237–46

Donahue B A, Augot M, Bellon S F, Treiber D K, Toney J H, Lippard S J and Essigmann J M (1990) Characterization of a DNA Damage-Recognition Protein from Mammalian Cells That Binds Specifically to Intrastrand d(GpG) and d(ApG) DNA Adducts of the Anticancer Drug Cisplatin. Biochemistry 29, 5872–5880.

Duguid J G, Li C, Shi M, Logan M J, Alila H, Rolland A, Tomlinson E, Sparrow J T, Smith L C (1998) A physicochemical approach for predicting the effectiveness of peptide-based gene delivery systems for use in plasmid-based gene therapy. Biophys J, 74(6):2802–14

Eapen S, Green M, Ismail I M (1985) Kinetic studies on the diaqua form of cis-platin and various nucleobases. J Inorg Biochem, 24(3):232–7

Eliopoulos A G, Kerr D J, Herod J, Hodgkins L, Krajewski S, Reed J C, Young L S (1995a) The control of apoptosis and drug resistance in ovarian cancer: influence of p53 and Bcl-2. Oncogene, 11 (7):1217–28

Eliopoulos A G, Kerr D J, Maurer H R, Hilgard P, Spandidos D A (1995b) Induction of the c-myc but not the cH-ras promoter by platinum compounds. Biochem Pharmacol, 50(1):33–8

Farhood H, Gao X, Son K, Yang Y Y, Lazo J S, Huang L, Barsoum J, Bottega R, Epand R M (1994) Cationic liposomes for direct gene transfer in therapy of cancer and other diseases. Ann N Y Acad Sci, 716:23–34; discussion 34–5

Fresta M, Chillemi R, Spampinato S, Sciuto S, Puglisi G (1998) Liposomal delivery of a 30-mer antisense oligodeoxynucleotide to inhibit proopiomelanocortin expression. J Pharm Sci, 87(5):616–25

Ghosh J K, Shai Y (1 999) Direct Evidence that the N-Terminal Heptad Repeat of Sendai Virus Fusion Protein Participates in Membrane Fusion. J Mol Biol, 292(3):531–546

Green M and Loewenstein P M (1988) Autonomous functional domains of chemically synthesized human immunodeficiency virus tat transactivator protein. Cell 55, 1179–1188.

Gupta D, Kothekar V (1997) 500 picosecond molecular dynamics simulation of amphiphilic polypeptide Ac(LKKL)4 NHEt with 1,2 di-mysristoyl-sn-glycero-3-phosphorylcholinc (DMPC) molecules. Indian J Biochem Biophys, 34(6):501–11

Holler E, Bauer R, Bernges F (1992) Monofunctional DNA-platinum(II) adducts block frequently DNA polymerases. Nucleic Acids Res 1992 May 11;20(9): 2307–12

Hughes E N, Engelsberg B N and Billings P C (1992) Purification of Nuclear Proteins That Bind to Cisplatin-damaged DNA. J. Biol. Chem. 267, 13520–13527.

Judice J K, Tom J Y, Huang W, Wrin T, Vennari J, Petropoulos C J, McDowell R S (1997) Inhibition of HIV type 1 infectivity by constrained alpha-helical peptides: implications for the viral fusion mechanism. Proc Natl Acad Sci U S A, 94(25):13426–30

Kim J C, Lee M H, Choi S K (1998) Synthesis and antitumor evaluation of cis-(1,2-diaminoethane) dichloroplatinum (II) complexes linked to 5- and 6-methyleneuracil and -uridine analogues. Arch Pharm Res, 21(4):465–9

Kono K, Nishii H, Takagishi T (1993) Fusion activity of an amphiphilic polypeptide having acidic amino acid residues: generation of fusion activity by alpha-helix formation and charge neutralization. Biochim Biophys Acta, 1164(1):81–90

Lambert G, Decout A, Vanloo B, Rouy D, Duverger N, Kalopissis A, Vandekerckhove J, Chambaz J, Brasseur R, Rosseneu M (1998) The C-terminal helix of human apolipoprotein AII promotes the fusion of unilamellar liposomes and displaces apolipoprotein AI from high-density lipoproteins. Eur J Biochem, 253(1):328–38

Lee S, Aoki R, Oishi O, Aoyagi H, Yamasaki N (1992) Effect of amphipathic peptides with different alpha-helical contents on liposome-fusion. Biochim Biophys Acta, 1103(1):157–62

Lelkes P I, Lazarovici P (1988) Pardaxin induces aggregation but not fusion of phosphatidylserine vesicles. FEBS Lett, 230(1–2):131–6

Lins L, Thomas-Soumarmon A, Pillot T, Vandekerckhove J, Rosseneu M, Brasseur R (1999) Molecular determinants of the interaction between the C-terminal domain of Alzheimer's beta-amyloid peptide and apolipoprotein E alpha-helices. J Neurochem, 73(2): 758–69

Macosko J C, Kim C H, Shin Y K (1997) The membrane topology of the fusion peptide region of influenza hemagglutinin determined by spin-labeling EPR. J Mol Biol, 267(5):1139–48

Macreadie I G, Lowe M G, Curtain C C, Hewish D, Azad A A (1997) Cytotoxicity resulting from addition of HIV-1 Nef N-terminal peptides to yeast and bacterial cells. Biochem Biophys Res Commun, 232(3):707–11

Martin F and Boulikas T (1998) The challenge of liposomes in gene therapy. Gene Ther Mol Biol 1, 173–214.

Martin I, Pecheur E I, Ruysschaert J M, Hoekstra D (1999) Membrane fusion induced by a short fusogenic peptide is assessed by its insertion and orientation into target bilayers. Biochemistry, 38(29):9337–47

Martin I, Ruysschaert J M (1997) Comparison of lipid vesicle fusion induced by the putative fusion peptide of fertilin (a protein active in sperm-egg fusion) and the NH2-terminal domain of the HIV2 gp41. FEBS Lett, 405(3):351–5

Massari S, Colonna R (1986) Gramicidin induced aggregation and size increase of phosphatidylcholine vesicles. Chem Phys Lipids, 39(3):203–20

McLaughlin K, Coren G, Masters J, Brown R (1993) Binding activities of cis-platin-damage-recognition proteins in human tumour cell lines. Int J Cancer, 53(4):662–6

Melino S, Rufini S, Sette M, Morero R, Grottesi A, Paci M, Petruzzelli R (1999) Zn(2+) ions selectively induce antimicrobial salivary peptide histatin-5 to fuse negatively charged vesicles. Identification and characterization of a zinc-binding motif present in the functional domain. Biochemistry, 38(30):9626–33

Midoux P, Monsigny M (1999) Efficient gene transfer by histidylated polylysine/pDNA complexes. Bioconjug Chem, 10(3):406–11

Morikawa K, Honda M, Endoh K, Matsumoto T, Akamatsu K, Mitsui H, Koizumi M (1990) Synthesis of platinum complexes of 2-aminomethylpyrrolidine derivatives for use as carrier ligands and their antitumor activities. Chem Pharm Bull (Tokyo), 38(4):930–5

Morikawa K, Honda M, Endoh K, Matsumoto T, Akamatsu K, Mitsui H, Koizumi M (1990) Synthesis of platinum complexes of 2-aminomethylpyrrolidine derivatives for use as carrier ligands and their antitumor activities. Chem Pharm Bull (Tokyo), 38(4):930–5

Murata M, Kagiwada S, Hishida R, Ishiguro R, Ohnishi S, Takahashi S (1991) Modification of the N-terminus of membrane fusion-active peptides blocks the fusion activity. Biochem Biophys Res Commun, 179(2): 1050–5

Mymryk J S, Zaniewski E and Archer T K (1995) Cisplatin inhibits chromatin remodeling, transcription factor binding, and transcription from the mouse mammary tumor virus promoter in vivo. Proc Natl Acad Sci USA 92, 2076–2080.

Niidome T, Kimura M, Chiba T, Ohmori N, Mihara H, Aoyagi H (1997) Membrane interaction of synthetic peptides related to the putative fusogenic region of PH-30 alpha, a protein in sperm-egg fusion. J Pept Res, 49(6):563–9

Oliver T and Mead G (1993) Testicular cancer. Curr Opin Oncol 5, 559–567.

Ormerod M G, O'Neill C, Robertson D, Kelland L R, Harrap K R (1996) cis-Diamminedichloroplatinum(II)-induced cell death through apoptosis in sensitive and resistant human ovarian carcinoma cell lines. Cancer Chemother Pharmacol, 37(5):463–71

Pak C C, Erukulla R K, Ahl P L, Janoff A S, Meers P (1999) Elastase activated liposomal delivery to nucleated cells. Biochim Biophys Acta, 1419(2): 111–26

Papadopoulou M V, Ji M, Bloomer W D (1998) NLCQ-1, a novel hypoxic cytotoxin: potentiation of melphalan, cisDDP and cyclophosphamide in vivo. Int J Radiat Oncol Biol Phys, 42(4):775–9

Parente R A, Nir S, Szoka F C Jr (1988) pH-dependent fusion of phosphatidylcholine small vesicles. Induction by a synthetic amphipathic peptide. J Biol Chem, 263(10):4724–30

Partidos C D, Vohra P, Steward M W (1996) Priming of measles virus-specific CTL responses after immunization with a CTL epitope linked to a fusogenic peptide. Virology, 215(l):107–10

Pecheur E I, Hoekstra D, Sainte-Marie J, Maurin L, Bienvenue A, Philippot J R (1997) Membrane anchorage brings about fusogenic properties in a short synthetic peptide. Biochemistry, 36(13):3773–81

Peelman F, Vanloo B, Perez-Mendez O, Decout A, Verschelde J L, Labeur C, Vinaimont N, Verhee A, Duverger N, Brasseur R, Vandekerckhove J, Tavernier J, Rosseneu M (1999) Characterization of functional residues in the interfacial recognition domain of lecithin cholesterol acyltransferase (LCAT). Protein Eng, 12(1):71–8

Pereira F B, Goni F M, Muga A, Nieva J L (1997) Permeabilization and fusion of uncharged lipid vesicles induced by the HIV-1 fusion peptide adopting an extended conformation: dose and sequence effects. Biophys J, 73(4):1977–86

Pil P M and Lippard S J (1992) Specific Binding of Chromosomal Protein HMG1 to DNA Damaged by the Anticancer Drug Cisplatin. Science 256, 234–237.

Pillot T, Drouet B, Queille S, Labeur C, Vandekerchkhove J, Rosseneu M, Pincon-Raymond M, Chambaz J (1999) The nonfibrillar amyloid beta-peptide induces apoptotic neuronal cell death: involvement of its C-terminal fusogenic domain. J Neurochem, 73(4): 1626–34

Pillot T, Goethals M, Vanloo B, Lins L, Brasseur R, Vandekerckhove J, Rosseneu M (1997a) Specific modulation of the fusogenic properties of the Alzheimer beta-amyloid peptide by apolipoprotein E isoforms. Eur J Biochem, 243(3):650–9

Pillot T, Lins L, Goethals M, Vanloo B, Baert J, Vandekerckhove J, Rosseneu M, Brasseur R (1997b) The 118–135 peptide of the human prion protein forms amyloid fibrils and induces liposome fusion. J Mol Biol, 274(3):381–93

Prasad K N, Hernandez C, Edwards-Prasad J, Nelson J, Borus T, Robinson W A (1994) Modification of the effect of tamoxifen, cis-platin, DTIC, and interferon-alpha 2b on human melanoma cells in culture by a mixture of vitamins. Nutr Cancer, 22(3):233–45

Rodriguez-Crespo I, Gomez-Gutierrez J, Nieto M, Peterson D L, Gavilanes F (1994) Prediction of a putative fusion peptide in the S protein of hepatitis B virus. J Gen Virol, 75 (Pt 3):637–9

Rodriguez-Crespo I, Nunez E, Yelamos B, Gomez-Gutierrez J, Albar J P, Peterson D L, Gavilanes F (1999) Fusogenic activity of hepadnavirus peptides corresponding to sequences downstream of the putative cleavage site. Virology, 261(1):133–42

Roth, J. A. et al. (1996), "Retrovius-mediated wild-type p53 gene transfer to tumors of patients with lung cancer" Nature Med. 2:985–991.

Schroth-Diez B, Ponimaskin E, Reverey H, Schmidt M F, Herrmann A (1998) Fusion activity of transmembrane and cytoplasmic domain chimeras of the influenza virus glycoprotein hemagglutinin. J Virol, 72(1):133–41

Stathopoulos G P, Rigatos S, Malamos N A (1999) Paclitaxel combined with cis-platin as second-line treatment in patients with advanced non-small cell lung cancers refractory to cis-platin. Oncol Rep, 6(4):797–800

Suenaga M, Lee S, Park N G, Aoyagi H, Kato T, Umeda A, Amako K (1989) Basic amphipathic helical peptides induce destabilization and fusion of acidic and neutral liposomes. Biochim Biophys Acta, 981(1): 143–50

Toney J H, Donahue B A, Kellett P J, Bruhn S L, Essigmann J M and Lippard S J (1989) Isolation of cDNAs encoding a human protein that binds selectively to DNA modified by the anticancer drug cis-diammine-dichloroplatinum(II). Proc Natl Acad Sci USA 86, 8328–8332.

Tournois H, Fabrie C H, Burger K N, Mandersloot J, Hilgers P, van Dalen H, de Gier J, de Kruijff B (1990) Gramicidin A induced fusion of large unilamellar dioleoylphosphatidylcholine vesicles and its relation to the induction of type II nonbilayer structures. Biochemistry, 29(36):8297–307

Ulrich A S, Tichelaar W, Forster G, Zschornig O, Weinkauf S, Meyer H W (1999) Ultrastructural characterization of peptide-induced membrane fusion and peptide self-assembly in the lipid bilayer. Biophys J, 77(2):829–41

Vergote I, Himmelmann A, Frankendal B, Scheistroen M, Viachos K, Trope C (1992) Hexamethylmelamine as second-line therapy in platin-resistant ovarian cancer. Gynecol Oncol, 47(3):282–286.

Vilpo J A, Vilpo L M, Szymkowski D E, O'Donovan A and Wood R D (1995) An XPG DNA repair defect causing mutagen hypersensitivity in mouse leukemia L1210 cells. Mbl Cell Biol 15, 290–297.

Voneche V, Callebaut I, Kettmann R, Brasseur R, Bumy A, Portetelle D (1992) The 19–27 amino acid segment of gp51 adopts an amphiphilic structure and plays a key role in the fusion events induced by bovine leukemia virus. J Biol Chem, 267(21):15193–7.

Zhang Y Q, Jiang X T, Sun Q R, Zhang G Q, Wang Y (1995) Studies on CDDP-albumin microspheres for hepatic arterial chemoembolization. Yao Hsueh Hsueh Pao, 30(7):543–8 [Article in Chinese].

What is claimed is:

1. A method for producing cisplatin micelles, comprising:
   a) combining a suitable buffer solution, cisplatin with an effective amount of at least a 30% ethanol solution to form a cisplatin/ethanol solution; and
   b) combining the solution with a negatively charged phosphatidyl glycerol lipid derivative wherein the molar ratio between cisplatin and the lipid derivative is 1:1 to 1:2, thereby producing a cisplatin mixture in its aqua form in micelles.

2. A method of producing cisplatin micelles, comprising:
   a) combining a suitable buffer solution, cisplatin with an effective amount of at least 30% ethanol solution to form a cisplatin/ethanol solution; and
   b) combining the cisplatin/ethanol solution with a negatively charged phosphatidyl glycerol lipid derivative wherein the molar ratio between cisplatin and the lipid derivative is 1:1 to 1:2, thereby producing a cisplatin mixture in its aqua form in micelles.

3. The method of claim 1 or 2, wherein the phosphatidyl glycerol lipid derivative is selected from the group consisting of dipalmitoyl phosphatidyl glycerol (DPPG), dimyristoyl phosphatidyl glycerol (DMPG), dicaproyl phosphatidyl glycerol (DCPG), distearoyl phosphatidyl glycerol (DSPG) and dioleyl phosphatidyl glycerol (DOPG).

4. The method of claim 1 or 2, wherein the molar ratio is 1:1.

5. The method of claim 1 or 2, further comprising combining an effective amount of a free fusogenic peptide, a fusogenic peptide-lipid conjugate or a fusogenic peptide—PEG-HSPC conjugate to the mixture of step a) where the fusogenic peptide is derivatized with a stretch of 1–6 negatively-charged amino acids at the N or C-terminus and thus, able to bind electrostatically to the cisplatin mixture in its aqua form.

6. The method of claim 5, wherein the free fusogenic peptide or fusogenic peptide lipid conjugate comprises DOPE or DOPE/cationic lipid.

7. The cisplatin micelle obtained by the method of claim 5.

8. The cisplatin micelle obtained by the method of claim 1 or 2.

9. A method for penetrating the cell membrane of a tumor cell in a subject comprising administering an effective amount of the cisplatin micelle obtainable by the method of claim 8.

10. A method for encapsulating cisplatin micelles, comprising mixing an effective amount of a vesicle-fonming lipid with the cisplatin micelles of claim 1 or 2.

11. The encapsulated cisplatin lipid micelle obtainable by the method of claim 10.

12. A method for obtaining a cisplatin/lipid complex capable of evading macrophages and cells of the immune system when administered to a subject, the method comprising mixing an effective amount of the cisplatin micelles of claim 11 with an effective amount of lipid selected from the group consisting of PEG-DSPE, PEG-DSPC and hyaluronic acid—DSPE.

13. An encapsulated cisplatin/lipid complex obtainable by the method of claim 12.

14. A method for delivering cisplatin to a cell comprising contacting the cell with the encapsulated cisplatin/lipid complex of claim 13.

15. A method for inhibiting the growth of a tumor in a subject, comprising administering to the subject an effective amount of the encapsulated cisplatin/lipid complex of claim 13.

16. A composition comprising the encapsulated cisplatin micelle of claim 11 and encapsulated oligonucleotides, ribozymes, triplex, PNA.

17. A composition comprising the encapsulated cisplatin micelle of claim 11 and a drug selected from the group consisting of doxorubicin, fluorodeoxyuridine, bleomycin, adriamycin, vinblastin, prednisone, vincristine, taxol.

18. The method of claim 10, wherein the lipid is selected from the group consisting of pre-made neutral liposomes comprising 10%–60% cholesterol, 40–90% hydrogenated soy phosphatidylcholine (HSPC), 1–7% polyethyleucglycol (PEG)-HSPC and PEG-DSPE.

19. An encapsulated cisplatin lipid micelle obtainable by the method of claim 18.

20. A method for delivering cisplatin to a cell comprising contacting the cell with the encapsulated cisplatin lipid micelle of claim 19.

21. A method for inhibiting the growth of a tumor in a subject, comprising administering to the subject an effective amount of the encapsulated cisplatin lipid micelle of claim 19.

22. A method for targeting solid tumors and metastases in a subject comprising intravenous administration of an effective amount of the encapsulated cisplatin micelle of claim 19 or the cisplatin/lipid complex of claim 13.

23. The method of claim 10, wherein the lipid comprises 10–60% cholesterol.

24. The method of claim 10, wherein the vesicle-forming lipid is in solution or powder form.

25. The method of claim 1 or 2, further comprising removal of the ethanol from the cisplatin micelles.

26. The method of claim 25, wherein removal of the ethanol is by dialysis of the cisplatin micelles through permeable membranes to remove the ethanol.

\* \* \* \* \*

SEQUENCE LISTING

<160> NUMBER OF SEQ ID NOS: 10

<210> SEQ ID NO 1
<211> LENGTH: 24
<212> TYPE: PRT
<213> ORGANISM: Influenza virus hemagglutinin HA-2

```
<400> SEQUENCE: 1

Gly Leu Phe Glu Ala Ile Ala Gly Phe Ile Glu Asn Gly Trp Glu Gly
1               5                   10                  15

Met Ile Asp Gly Gly Gly Tyr Cys
            20

<210> SEQ ID NO 2
<211> LENGTH: 11
<212> TYPE: PRT
<213> ORGANISM: Human Immunodeficiency Virus

<400> SEQUENCE: 2

Tyr Gly Arg Lys Lys Arg Arg Gln Arg Arg Arg
1               5                   10

<210> SEQ ID NO 3
<211> LENGTH: 20
<212> TYPE: PRT
<213> ORGANISM: Artificial Sequence
<220> FEATURE:
<223> OTHER INFORMATION: A fusion peptide formulated with DNA plasmids
      to create peptide-based gene delivery systems.

<400> SEQUENCE: 3

Gly Leu Phe Glu Ala Leu Leu Glu Leu Leu Glu Ser Leu Trp Glu Leu
1               5                   10                  15

Leu Leu Glu Ala
            20

<210> SEQ ID NO 4
<211> LENGTH: 16
<212> TYPE: PRT
<213> ORGANISM: Duck Hepatitis B Virus

<400> SEQUENCE: 4

Met Ser Gly Thr Phe Gly Gly Ile Leu Ala Gly Leu Ile Gly Leu Leu
1               5                   10                  15

<210> SEQ ID NO 5
<211> LENGTH: 16
<212> TYPE: PRT
<213> ORGANISM: Woodchuck hepatitis B virus

<400> SEQUENCE: 5

Met Ser Pro Ser Ser Leu Leu Gly Leu Leu Ala Gly Leu Gln Val Val
1               5                   10                  15

<210> SEQ ID NO 6
<211> LENGTH: 20
<212> TYPE: PRT
<213> ORGANISM: Artificial Sequence
<220> FEATURE:
<223> OTHER INFORMATION: An amphipathic peptide.

<400> SEQUENCE: 6

Gly Leu Phe Glu Ala Leu Leu Glu Leu Leu Glu Ser Leu Trp Glu Leu
1               5                   10                  15

Leu Leu Glu Ala
            20

<210> SEQ ID NO 7
<211> LENGTH: 16
<212> TYPE: PRT
<213> ORGANISM: Artificial Sequence
```

```
<220> FEATURE:
<223> OTHER INFORMATION: An amphiphilic fusogenic peptide.

<400> SEQUENCE: 7

Leu Lys Lys Leu Leu Lys Lys Leu Leu Lys Lys Leu Leu Lys Lys Leu
 1               5                  10                  15

<210> SEQ ID NO 8
<211> LENGTH: 12
<212> TYPE: PRT
<213> ORGANISM: Artificial Sequence
<220> FEATURE:
<223> OTHER INFORMATION: Basic amphipathic peptide.

<400> SEQUENCE: 8

Leu Ala Arg Leu Leu Ala Arg Leu Leu Ala Arg Leu
 1               5                  10

<210> SEQ ID NO 9
<211> LENGTH: 28
<212> TYPE: PRT
<213> ORGANISM: Artificial Sequence
<220> FEATURE:
<223> OTHER INFORMATION: 30 amino acid peptide with the major repeat
      sequence of this sequence, designed to mimic the
      behavior of the fusogenic sequences of viral
      fusion proteins.

<400> SEQUENCE: 9

Gly Ala Leu Ala Gly Ala Leu Ala Gly Ala Leu Ala Gly Ala Leu Ala
 1               5                  10                  15

Gly Ala Leu Ala Gly Ala Leu Ala Gly Ala Leu Ala
            20                  25

<210> SEQ ID NO 10
<211> LENGTH: 4
<212> TYPE: PRT
<213> ORGANISM: Artificial Sequence
<220> FEATURE:
<223> OTHER INFORMATION: Fusogenic peptide.

<400> SEQUENCE: 10

Ala Ala Pro Val
 1
```